United States Patent
Dunn-Coleman et al.

(10) Patent No.: US 7,074,608 B1
(45) Date of Patent: Jul. 11, 2006

(54) METHOD FOR THE PRODUCTION OF 1,3-PROPANEDIOL BY RECOMBINANT ORGANISMS COMPRISING GENES FOR COENZYME $B_{12}$ SYNTHESIS

(75) Inventors: Nigel S. Dunn-Coleman, Los Gatos, CA (US); Anthony A. Gatenby, Wilmington, DE (US); Fernando Valle, Burlingame, CA (US)

(73) Assignees: E. I. du Pont de Nemours and Company, Wilmington, DE (US); Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/310,001

(22) Filed: May 11, 1999

Related U.S. Application Data

(60) Provisional application No. 60/085,214, filed on May 12, 1998.

(51) Int. Cl.
*C12N 1/20* (2006.01)
(52) U.S. Cl. ............................. 435/252.33; 435/254.11; 435/252.3; 435/419; 435/325
(58) Field of Classification Search ................ 435/325, 435/419, 254.11, 252.3, 252.33
See application file for complete search history.

(56) References Cited

U.S. PATENT DOCUMENTS

| | | | |
|---|---|---|---|
| 5,599,689 A | 2/1997 | Haynie et al. | 435/42 |
| 5,633,362 A | 5/1997 | Nagarajan et al. | 536/23.1 |
| 5,686,279 A | 11/1997 | Finer et al. | 435/172.3 |
| 6,013,494 A * | 1/2000 | Nakamura et al. | |

FOREIGN PATENT DOCUMENTS

| | | |
|---|---|---|
| EP | 0 516 647 B1 | 12/1998 |
| WO | WO 87/01391 | 3/1987 |
| WO | WO98/21339 | 5/1998 |
| WO | WO 98/21340 | 5/1998 |
| WO | WO 98/21341 | 5/1998 |

OTHER PUBLICATIONS

Suh et al. Cloning, sequencing and overexpression of cobA which encodes ATP:corrinoid adenosyltransferase in Salmonella typhimurium. Gene (1993) 129:93-97.*
Bobik et al. Propanediol utilization genes (pdu) of Salmonella typhimurium: three genes for the propanediol dehydratase. J. Bacteriology (1997) 179(21):6633-6639.*
GenBank Accession No. AE008776. Salmonella typhimurium LT2, section 84 of 224 of the complete genome. (2001).*
GenBank Accession No. AAL20944. Propanediuol utilization dehydratase, large subunit [Salmonella typhimurium LT2]. 2001.*
GenBank Accession No. ECU17433. *Escherichia coli*, putative dehydrogenase and putative oxidoreductase (yciK) genes, complete cds, and (btuR) and (sohB) genes, 5'UTR. (1944).*
Skraly et al. Construction and Characterization of a 1,3-Propanediol Operon. Applied and Environmental Microbiology (Jan., 1998) 64(1): 98-105.*
Crouzet et al., Genetic and Sequence Analysis of an 8.7 Kilobase *Pseudomonas denitrificans* Fragment Carrying Eight Genes Involved in Transformation of Precorrin-2 to Cobyrinic Acid, Journal of Bacteriology, Oct. 1990, vol. 172, No. 19, p. 5980-5990.
Cameron et al., Cloning and Analysis of Genes Involved in Coenzyme $B_{12}$ Biosynthesis in *Pseudomonas denitrificans*, Journal of Bacteriology, Jan. 1989, vol. 14, pp. 547-557.
Blanche et al., Purification and Characterization of S-Adenosyl-L-Methionine: Uroporphyrinogen III Methyltransferase from *Pseudomonas dennitrificans*, Journal of Bacteriology, Aug. 1989, pp. 4222-4231, vol. 171, No. 8.
Jeter et al., Cobalamin (Vitamin B12) Biosynthetic Genes of *Salmonella typhimurium*, Journal of Bacteriology., Jul. 1987, vol. 169, No. 7, 3189-3198.
Crouzet et al., Nucleotide Sequence of a *Pseudomonas denitrificans* 5,4-Kilobase DNA Fragment Containing Five cob Genes and Identification of Structural Genes Encoding S-Adenosyl-L-Methionine: Journal of Bacteriology, vol. 172, No. 10 p. 5968-5979, Oct. 1990.

* cited by examiner

*Primary Examiner*—Tekchand Saidha

(57) ABSTRACT

Recombinant organisms are provided comprising genes encoding aquacobalamin reductase, cob(II)alamin reductase, cob(I)alamin adenosyltransferase, glycerol dehydratase and 1,3-propanediol oxidoreductase activities useful for the production of 1,3-propanediol from a variety of carbon substrates. More specifically the following nucleotide sequences are provided: btuR, encoding the *E. coli* cob(I) alamin adenosyltransferase enzyme; cobA, encoding the *Salmonella typhimurium* cob(I)alamin adenosyltransferase enzyme; cobO, encoding the *Pseudomonas denitrificans* cob(I)alamin adenosyltransferase enzyme; dhaB1, encoding the α subunit of the *Klebsiella* glycerol dehydratase enzyme; dhaB2, encoding the β subunit of the *Klebsiella* glycerol dehydratase enzyme; dhaB3, encoding the γ subunit of the *Klebsiella* glycerol dehydratase enzyme; dhaT, encoding *Klebsiella* oxidoreductase enzyme; the yciK gene isolated from *E. coli*; the glucose isomerase promoter sequence from *Streptomyces*; and the N-terminal amino acid sequence for cob(II)alamin reductase from *Pseudomonas denitrificans*.

1 Claim, No Drawings

METHOD FOR THE PRODUCTION OF 1,3-PROPANEDIOL BY RECOMBINANT ORGANISMS COMPRISING GENES FOR COENZYME $B_{12}$ SYNTHESIS

CROSS-REFERENCE TO RELATED APPLICATION

This application claims priority to the U.S. Provisional Application No. 60/085,214 filed on May 12, 1998.

FIELD OF INVENTION

The present invention relates to the field of molecular biology and the use of recombinant organisms for the production of 1,3-propanediol. More specifically it describes the expression of cloned genes that affect the transformation of coenzyme $B_{12}$ precursors to coenzyme $B_{12}$ in conjunction with genes that effectively convert a carbon substrate to 1,3-propanediol.

BACKGROUND 1,3-Propanediol is a monomer useful in the production of polyester fibers and the manufacture of polyurethanes and cyclic compounds.

A variety of chemical routes to 1,3-propanediol are known. For example, 1,3-propanediol is prepared from 1) ethylene oxide over a catalyst in the presence of phosphine, water, carbon monoxide, hydrogen and an acid; 2) by the catalytic solution phase hydration of acrolein followed by reduction; or 3) from hydrocarbons such as glycerol, reacted in the presence of carbon monoxide and hydrogen over catalysts having atoms from Group VIII of the periodic table. Although it is possible to generate 1,3-propanediol by these chemical methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups *Citrobacter, Clostridium, Enterobacter, Ilyobacter, Klebsiella, Lactobacillus,* and *Pelobacter*. In each case studied, glycerol is converted to 1,3-propanediol in a two-step, enzyme-catalyzed reaction sequence. In the first step, a dehydratase catalyzes the conversion of glycerol to 3-hydroxypropionaldehyde (3-HP) and water (Equation 1). In the second step, 3-HP is reduced to 1,3-propanediol by a NAD$^+$-linked oxidoreductase (Equation 2).

Glycerol→3-HP+H$_2$O (Equation 1)

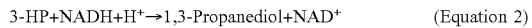

3-HP+NADH+H$^+$→1,3-Propanediol+NAD$^+$ (Equation 2)

The 1,3-propanediol is not metabolized further and, as a result, accumulates in high concentration in the media. The overall reaction consumes a reducing equivalent in the form of a cofactor, reduced β-nicotinamide adenine dinucleotide (NADH), which is oxidized to nicotinamide adenine dinucleotide (NAD$^+$).

The production of 1,3-propanediol from glycerol is generally performed under anaerobic conditions using glycerol as the sole carbon source and in the absence of other exogenous reducing equivalent acceptors. For example, in strains of *Citrobacter, Clostridium,* and *Klebsiella*, a parallel pathway for glycerol operates under these conditions which first involves oxidation of glycerol to dihydroxyacetone (DHA) by a NAD$^+$- (or NADP$^+$-) linked glycerol dehydrogenase (Equation 3). The DHA, following phosphorylation to dihydroxyacetone phosphate (DHAP) by a DHA kinase (Equation 4), becomes available for biosynthesis and for supporting ATP generation via, for example, glycolysis.

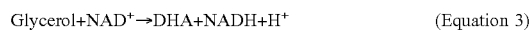

Glycerol+NAD$^+$→DHA+NADH+H$^+$ (Equation 3)

DHA+ATP→DHAP+ADP (Equation 4)

In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulons from *Citrobacter* and *Klebsiella* have been expressed in *Escherichia coli* and have been shown to convert glycerol to 1,3-propanediol.

The biological production of 1,3-propanediol requires glycerol as a substrate for a two-step sequential reaction in which a dehydratase enzyme (typically a coenzyme $B_{12}$-dependent dehydratase) converts glycerol to an intermediate, 3-hydroxypropionaldehyde, which is then reduced to 1,3-propanediol by a NADH- (or NADPH) dependent oxidoreductase. The complexity of the cofactor requirements necessitates that a whole cell catalyst be used for an industrial process incorporating this reaction sequence for the production of 1,3-propanediol. A process for the production of 1,3-propanediol from glycerol using an organism containing a coenzyme $B_{12}$-dependent diol dehydratase is described in U.S. Pat. No. 5,633,362 (Nagarajan et al.). However, the process is not limited to the use of glycerol as feedstock. Glucose and other carbohydrates are suitable substrates and, recently, these substrates have been shown to be substrates for 1,3-propanediol production. Carbohydrates are converted to 1,3-propanediol using mixed microbial cultures where the carbohydrate is first fermented to glycerol by one microbial species and then converted to 1,3-propanediol by a second microbial species U.S. Pat. No. 5,599,689 (Haynie et al.). However, a single organism able to convert carbohydrates to 1,3-propanediol is preferred for reasons of simplicity and economy. Such an organism is described in U.S. Pat. No. 5,686,276 (Laffend et al.); and in U.S. Pat. No. 6,136,576 (Diaz-Torres et al.).

Glycerol dehydratase and diol dehydratase are coenzyme $B_{12}$-dependent enzymes which catalyze the conversion of glycerol to 3-HP (Toraya, T., In *Metalloenzymes Involving Amino Acid-Residue and Related Radicals*; Sigel, H. and Sigel, A., Eds.; Metal Ions in Biological Systems; Marcel Dekker: New York, 1994; Vol. 30, pp 217–254). Coenzyme $B_{12}$ may be provided by the whole cell catalyst through de novo synthesis. However, if the coenzyme $B_{12}$ requirement of the $B_{12}$-dependent dehydratases exceeds the de novo synthesis capacity of the whole cell catalyst or if the whole cell catalyst lacks the de novo synthesis capacity, then coenzyme $B_{12}$ or coenzyme $B_{12}$ precursors may be provided in the reaction medium. Due to the cost and instability of coenzyme $B_{12}$, medium supplementation with coenzyme $B_{12}$ precursors is preferred; and this then requires the conversion of these precursors to coenzyme $B_{12}$. In addition, glycerol dehydratase and diol dehydratase undergo inactivation which involves loss of the 5'-deoxyadenosyl moiety from coenzyme $B_{12}$ and the formation of hydroxocobalamin and/or cob(II)alamin. (Toraya, T., supra.) Thus, readenosylation of hydroxocobalamin and/or cob(II)alamin is required for the recycling of coenzyme $B_{12}$.

Vitamin $B_{12}$ (cyanocobalamin) and hydroxocobalamin are stable, commercially available coenzyme $B_{12}$ precursors which are readily taken up by microorganisms. Conversion of these precursors, both Co(III) species, to coenzyme $B_{12}$ (5'-deoxyadenosyl cobalamin) involves: 1.) reduction of Co(III) to Co(II) (i.e., formation of cob(II)alamin by a aquacobalamin reductase), 2.) reduction of Co(II) to Co(I) (i.e., formation of cob(I)alamin by a cob(II)alamin reductase), and 3.) ATP-dependent adenosylation of cob(I)alamin by a cob(I)alamin adenosyltransferase to form coenzyme $B_{12}$. Enzymes associated with these functions have been described for *Salmonella typhimurium*, *Pseudomonas denitrificans*, and *Clostridium tetanomorphum*. Suh and Escalante-Semerena, *J. Bacteriol.* 177, 921–925 (1995) and references therein. Similar systems have been described for *Euglena gracilis* (Watanabe et al., *Arch. Biochem. Biophys.* 305, 421–427 (1993)), *Chlamydomonas reinhardtii* (Watanabe et al., *Biochim. Biophys. Acta* 1075, 36–41 (1991)), and mammalian cells (Pezacka, E. H., *Biochim. Biophys. Acta* 1157, 167–177 (1993)).

The problem to be solved is how to biologically produce 1,3-propanediol by a single recombinant organism containing genes facilitating the synthesis of $B_{12}$ coenzyme in the presence of a $B_{12}$-dependent dehydratase enzyme.

SUMMARY OF THE INVENTION

Applicants have solved the stated problem. They provide a single organism capable of the dehydratase-mediated bioconversion of a fermentable carbon source directly to 1,3-propanediol, where $B_{12}$ coenzyme synthesis is effected by foreign genes encoding aquacobalamin reductase, cob (II)alamin reductase and cob(I)alamin adenosyltransferase activities. Glucose and glycerol are used as model substrates and the bioconversion is applicable to any existing microorganism.

The present invention provides a process for the production of 1,3-propanediol from a transformed host cell comprising (i) contacting a transformed host cell with at least one fermentable carbon source and an effective amount of coenzyme $B_{12}$ precursor whereby 1,3-propanediol is produced; wherein said host cell comprises: a) at least one copy of a gene encoding a protein having a dehydratase activity; b) at least one copy of a gene encoding a protein having an oxidoreductase activity; c) at least one copy of a gene encoding a protein having a aquacobalamin reductase activity; d) at least one copy of a gene encoding a protein having a cob(II)alamin reductase activity; and e) at least one copy of a gene encoding a protein having a cob(I)alamin adenosyltransferase activity; wherein at least one of the genes of (c), (d) or (e) is introduced into the host cell, and (ii) recovering the 1,3-propanediol produced in (i). The dehydratase activity of (i)(a) may be from either a glycerol dehydratase enzyme or a diol dehydratase enzyme. The process may be regulated by selectively inhibiting any one of the genes of (i)(c), (i)(d), or (i)(e) to alter the metabolism of coenzyme $B_{12}$ precursor. The effective amount of coenzyme $B_{12}$ precursor is at a 0.1-to 10.0-fold molar ratio to the amount of dehydratase present, the improved production measured against a bioprocess where the genes are not present in multicopy.

The invention further provides a transformed host organism containing (a) at least one copy of a gene encoding a protein having a dehydratase activity; (b) at least one gene encoding a protein having an oxidoreductase activity; (c) at least one copy of a gene encoding a protein having an aquacobalamin reductase activity; (d) at least one copy of a gene encoding a protein having a cob(II)alamin reductase activity; (e) and at least one copy of a gene encoding a protein having a cob(I)alamin adenosyltransferase activity, wherein at least one of the genes of (i)(c), (i)(d), or (i)(e) is introduced into the host cell.

BRIEF DESCRIPTION OF SEQUENCE LISTING

Applicants have provided 26 sequences in conformity with Rules for the Standard Representation of Nucleotide and Amino Acid Sequences in Patent Applications (Annexes I and II to the Decision of the President of the EPO, published in Supplement No. 2 to OJ EPO, 12/1992), with 37 C.F.R. 1.821–1.825 and Appendices A and B (Requirements for Application Disclosures Containing Nucleotides and/or Amino Acid Sequences) with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO:1 is the nucleotide sequence for btuR, encoding the *E. coli* cob(I)alamin adenosyltransferase enzyme.

SEQ ID NO:2 is the nucleotide sequence for cobA, encoding the *Salmonella typhimurium* cob(I)alamin adenosyltransferase enzyme.

SEQ ID NO:3 is the nucleotide sequence for cobO, encoding the *Pseudomonas denitrificans* cob(I)alamin adenosyltransferase enzyme.

SEQ ID NO:4 is the nucleotide sequence for dhaB1, encoding the α subunit of the *Klebsiella* glycerol dehydratase enzyme.

SEQ ID NO:5 is the nucleotide sequence for dhaB2, encoding the β subunit of the *Klebsiella* glycerol dehydratase enzyme.

SEQ ID NO:6 is the nucleotide sequence for dhaB3, encoding the γ subunit of the *Klebsiella* glycerol dehydratase enzyme.

SEQ ID NO:7 the nucleotide sequence for dhaT, encoding *Klebsiella* oxidoreductase enzyme.

SEQ ID NO:8 is a universal primer used in the isolation of the Cob(II)alamin reductase gene.

SEQ ID NO:9 is the nucleotide sequence for the yciK gene isolated from *E. coli*, encoding a cob(II)alamin reductase activity.

SEQ ID NO:10 is the nucleotide sequence for PHK28-26 a 12.1 kb EcoRI-SalI fragment containing the dha operon.

SEQ ID NO:11 is the nucleotide sequence for a multiple cloning site and terminator sequence used in the construction of the expression vector pTacIQ.

SEQ ID NO:12–19 are primers used in the construction of expression vectors of the present invention.

SEQ ID NO:20 is the nucleotide sequence for an insert in pCL1920, used in the construction of the expression cassette for dhaT and dhaB(1,2,3).

SEQ ID NO:21 is the nucleotide sequence for the glucose isomerase promoter sequence from *Streptomyces*.

SEQ ID NO:22–25 are primers used in the construction of expression vectors of the present invention.

SEQ ID NO:26 is the N-terminal amino acid sequence for cob(II)alamin reductase from *Pseudomonas denitrificans*.

DETAILED DESCRIPTION OF THE INVENTION

The present invention provides a method for biologically producing 1,3-propanediol from a fermentable carbon source in a single recombinant organism. The method incorporates a microorganism containing genes encoding glycerol dehydratase, 1,3-propanediol oxidoreductase, aquacobalamin reductase, cob(II)alamin reductase, and cob(I)alamin adenosyltransferase. The recombinant microorganism is contacted with a carbon substrate (preferably glucose or glycerol) and 1,3-propanediol is isolated from the growth media.

The present method provides a rapid, inexpensive and environmentally responsible source of 1,3-propanediol monomer useful in the production of polyesters and other polymers.

The following definitions are to be used to interpret the claims and specification.

The term "aquacobalamin reductase" refers to an enzyme responsible for the reduction of aquacobalamin to cob(II)alamin which involves the reduction of Co(III) to Co(II). Typical of aquacobalamin reductase is EC 1.6.99.8.

The term "cob(II)alamin reductase" refers to an enzyme responsible for the reduction of cob(II)alamin to cob(I)alamin which involves the reduction of Co(II) to Co(I). Typical of cob(II)alamin reductase is EC 1.6.99.9. For purposes of the present invention, the terms "aquacobalamin reductase" and "cob(II)alamin reductase" include those reductases which catalyze the corresponding reactions starting from vitamin $B_{12}$.

The term "cob(I)alamin adenosyltransferase" refers to an enzyme responsible for the transfer of a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" (GenBank M21528) (SEQ ID NO:1) in *Escherichia coli*, "cobA" (GenBank L08890) (SEQ ID NO:2) in *Salmonella typhimurium*, and "cobO" (SEQ ID NO3) (GenBank M62866) in *Pseudomonas denitrificans*.

The terms "coenzyme $B_{12}$" and "adenosylcobalamin" are used interchangeably to mean 5'-deoxyadenosylcobalamin. Hydroxocobalamin is the derivative of coenzyme $B_{12}$ where the upper axial 5'-deoxyadenosyl ligand is replaced with a hydroxy moiety. Aquacobalamin is the unprotonated form of hydroxocobalamin. The terms "vitamin $B_{12}$" and "cyanocobalamin" are used interchangeably and refer to the derivative of coenzyme $B_{12}$ where the upper axial 5'-deoxy'5'-adenosyl ligand is replaced with a cyano moiety. The term "coenzyme $B_{12}$ precursor" refers to a derivation of coenzyme $B_{12}$ where the upper axial 5'-deoxyadenosyl ligand is replaced. An "effective amount" of coenzyme $B_{12}$ precursor will mean that coenzyme $B_{12}$ precursor is present in the system at approximately a 0.1- to 10.0-fold molar ratio to the amount of dehydratase enzyme present.

The terms "glycerol dehydratase" or "dehydratase enzyme" refer to the polypeptide(s) responsible for a coenzyme $B_2$-dependent enzyme activity that is capable of isomerizing or converting a glycerol molecule to the product 3-hydroxypropionaldehyde. For the purposes of the present invention the dehydratase enzymes include a glycerol dehydratase (GenBank U09771, U30903) and a diol dehydratase (GenBank D45071) having preferred substrates of glycerol and 1,2-propanediol, respectively. Glycerol dehydratase of *K. pneumoniae* ATCC 25955 is encoded by the genes dhaB1, dhaB2, and dhaB3 identified as SEQ ID NOS:4, 5, and 6 respectively. The dhaB1, dhaB2 and dhaB3 genes code for the α, β, and γ subunits of the glycerol dehydratase enzyme, respectively. Glycerol dehydratase and diol dehydratase enzymes are complexes (with an $α_2β_2γ_2$ subunit composition) that bind coenzyme $B_{12}$ with a 1:1 stoichiometry.

An "effective amount" of coenzyme $B_{12}$ precursor (or vitamin $B_{12}$) will mean that coenzyme $B_{12}$ precursor (or vitamin $B_{12}$) is present in the system at a molar ratio of between 0.1 and 10, relative to the dehydratase enzyme.

The terms "oxidoreductase" or "1,3-propanediol oxidoreductase" refer to the polypeptide(s) responsible for an enzyme activity that is capable of catalyzing the reduction of 3-hydroxypropionaldehyde to 1,3-propanediol. 1,3-Propanediol oxidoreductase includes, for example, the polypeptide encoded by the dhaT gene (GenBank U09771, U30903) and is identified as SEQ ID NO:7.

The terms "polypeptide" and "protein" are used interchangeably.

The terms "fermentable carbon substrate" and "fermentable carbon source" refer to a carbon source capable of being metabolized by host organisms of the present invention and particularly carbon sources selected from the group consisting of monosaccharides, oligosaccharides, polysaccharides, glycerol, dihydroxyacetone and one-carbon substrates or mixtures thereof.

The terms "host cell" or "host organism" refer to a microorganism capable of receiving foreign or heterologous genes and of expressing those genes to produce an active gene product.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The terms "encoding" and "coding" refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue (such as glycine), or a more hydrophobic residue (such as valine, leucine, or isoleucine). Similarly, changes which result in substitution of one negatively charged residue for another (such as aspartic acid for glutamic acid), or one positively charged residue for another (such as lysine for arginine), can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "substantially similar" refers to the relationship between nucleic acid fragments wherein the second contains changes in one or more nucleotide bases relative to the first resulting in substitution of one or more amino acids, but with no affect on the functional properties of the protein encoded by the DNA sequence. "Substantially similar" also refers to the effect of modifications (such as deletion or insertion of one or more nucleotide bases) to the nucleic acid fragment of the instant invention that do not substantially affect the functional properties of the resulting transcript vis-à-vis the ability to mediate alteration of gene expression by antisense or co-suppression technology or of alteration of the functional properties of the resulting protein molecule. It is therefore understood that the invention encompasses more than the specific exemplary sequences.

For example, it is well-known that alterations in a gene which result in the production of a chemically equivalent amino acid at a given site may nevertheless not effect the functional properties of the encoded protein. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the identical to the DNA sequence of the nucleic acid fragments reported herein. Most preferred are nucleic acid fragments that are at least 95% identical to the DNA sequence of the nucleic acid fragments reported herein.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular reductase proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The term "genetically altered" refers to the process of changing hereditary material by transformation or mutation.

The term "regulate" refers to control of the production of 1,3-propanediol by selective inhibition of the genes encoding a protein having an aquacobalamin reductase activity, of the genes encoding a protein having a cob(II)alamin reductase activity, or of the genes encoding a protein having a cob(I)alamin adenosyltransferase activity.

The present invention involves the construction of a production organism that incorporates the genetic machinery necessary to convert a fermentable carbon substrate to 1,3-propanediol, in conjunction with genes encoding enzymes needed for the biotransformation of coenzyme $B_{12}$ precursor to coenzyme $B_{12}$. The genes involved in 1,3-propanediol production will include a dehydratase gene (typically a glycerol or diol dehydratase) and an oxidoreductase as well as other proteins expected to aid in the assembly or in maintaining the stability of the dehydratase enzyme. These genes may be transgenes and introduced into the host cell, or may be endogenous. Genes responsible for the conversion of coenzyme $B_{12}$ precursor to coenzyme $B_{12}$ will include at least one copy of a gene encoding a protein having a aquacobalamin reductase activity; at least one copy of a gene encoding a protein having a cob(II)alamin reductase activity, and at least one copy of a gene encoding a protein having a cob(I)alamin adenosyltransferase activity. At least one of these genes will be a transgene and introduced into the production cell. The transformed production cell is then grown under appropriate conditions for the production of 1,3-propanediol.

Recombinant organisms containing the necessary genes that will encode the enzymatic pathway for the conversion of a carbon substrate to 1,3-propanediol may be constructed using techniques well known in the art. In the present invention genes encoding glycerol dehydratase (dhaB) and 1,3-propanediol oxidoreductase (dhaT) were isolated from a native host such as *Klebsiella* and (together with genes encoding aquacobalamin reductase, cob(II)alamin reductase and cob(I)alamin adenosyltransferase (btuR or cobA or cobO) isolated from native hosts such as *E. coli*, *S. typhimurium* or *P. denitrificans*) are used to transform host strains such as *E. coli* strain DH5α or FM5; *K. pneumoniae* strain ATCC 25955; *K. oxytoca* strain ATCC 8724 or M5a1, *S. cerevisiae* strain YPH499, *P. pastoris* strain GTS 115, or *A. niger* strain FS1.

Rational for Using dhaB, dhaT

Producing 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or by reduction of DHAP to glycerol 3-phosphate (G3P) followed by hydrolysis. The hydrolysis step can be catalyzed by any number of cellular phosphatases which are known to be non-specific with respect to their substrates or the activity can be introduced into the host by recombination. The reduction step can be catalyzed by a NAD$^+$ (or NADP$^+$) linked host enzyme or the activity can be introduced into the host by recombination. It is notable that the dha regulon contains a glycerol dehydrogenase (E.C. 1.1.1.6) which catalyzes the reversible reaction of Equation 7.

Glycerol→3-HP+H$_2$O  (Equation 5)

3-HP+NADH+H$^+$→1,3-Propanediol+NAD$^+$  (Equation 6)

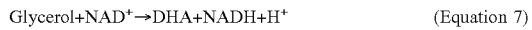

Glycerol+NAD$^+$→DHA+NADH+H$^+$  (Equation 7)

Glycerol is converted to 1,3-propanediol via the intermediate 3-hydroxy-propionaldehye (3-HP) as has been described in detail above. The intermediate 3-HP is produced from glycerol, Equation 5, by a dehydratase enzyme which can be encoded by the host or can introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HP, Equation 6, by a NAD$^+$- (or NADP$^+$) linked host enzyme or the activity can introduced into the host by recombination. This final reaction in the production of 1,3-propanediol can be catalyzed by 1,3-propanediol dehydrogenase (E.C. 1.1.1.202) or other alcohol dehydrogenases.

The dha regulon is comprised of several functional elements including dhaK encoding a dihydroxyacetone kinase, dhaD encoding a glycerol dehydrogenase, dhaR encoding a regulatory protein, dhaT encoding a 1,3-propanediol oxidoreductase as well as dhaB1, dhaB2, and dhaB3 encoding the alpha, beta and gamma subunits of a glycerol dehydratase, respectively. Additionally, gene products designated as protein X, protein 1, protein 2, and protein 3 (corresponding to dhaBX, orfY, orfX, and orfW, respectively) are encoded with the dha regulon. While the precise functions of these gene products are not well characterized, the genes are linked to glycerol dehydratase (dhaB) or 1,3-propanediol oxidoreductase (dhaT) and are known to be useful for the production of 1,3-propanediol. Coenzyme $B_{12}$ that is bound to glycerol dehydratase occasionally undergoes irreversible cleavage to form an inactive modified coenzyme which is tightly bound to the dehydratase. Reactivation of the enzyme occurs by exchange of the bound, modified coenzyme with free, intact coenzyme $B_{12}$. Protein X and at least one other of protein 1, protein 2, and protein 3 are involved in the exchange process. (see U.S. Pat. No. 6,136,576). In the separate diol dehydratase system, genes designated as ddrA and ddrB, corresponding to the genes encoding protein X and protein 2, respectively, are described to be involved in the exchange process (Mori et al., *J. Biol. Chem.* 272, 32034–32041 (1997)).

Glycerol-3-phosphate dehydrogenase and glycerol-3-phosphatase may be particularly effective in the conversion of glucose to glycerol, required for the production of 1,3-propanediol (U.S. Ser. No. 60/030,602). The term "glycerol-3-phosphate dehydrogenase" refers to a polypeptide responsible for an enzyme activity that catalyzes the conversion of dihydroxyacetone phosphate (DHAP) to glycerol-3-phosphate (G3P). In vivo G3PDH may be NADH-, NADPH-, or FAD-dependent. The NADH-dependent enzyme (EC 1.1.1.8) is encoded, for example, by several genes including GPD1 (GenBank Z74071×2), or GPD2 (GenBank Z35169x1), or GPD3 (GenBank G984182), or DAR1 (GenBank Z74071x2). The NADPH-dependent enzyme (EC 1.1.1.94) is encoded by gpsA (GenBank U321643, (cds 197911–196892) G466746 and L45246). The FAD-dependent enzyme (EC 1.1.99.5) is encoded by GUT2 (GenBank Z47047x23), or glpD (GenBank G147838), or glpABC (GenBank M20938). The term "glycerol-3-phosphatase" refers to a polypeptide responsible for an enzyme activity that catalyzes the conversion of glycerol-3-phosphate and water to glycerol and inorganic phosphate. Glycerol-3-phosphatase is encoded, for example, by GPP1 (GenBank Z47047x125), or GPP2 (GenBank U18813x11).

Gene Isolation

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, cosmid libraries may be created where large segments of genomic DNA (35–45 kb) may be packaged into vectors and used to transform appropriate hosts. Cosmid vectors are unique in being able to accommodate large quantities of DNA. Generally, cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook et al., *Molecular Cloning: A Laboratory Manual*, Second Edition (1989) Cold Spring Harbor Laboratory Press, Cold Spring Harbor, N.Y. (1989).

Typically to clone cosmids, foreign DNA is isolated and ligated, using the appropriate restriction endonucleases, adjacent to the cos region of the cosmid vector. Cosmid vectors containing the linearized foreign DNA are then reacted with a DNA packaging vehicle such as bacteriophage λ. During the packaging process the cos sites are cleaved and the foreign DNA are packaged into the head portion of the bacterial viral particle. These particles are then used to transfect suitable host cells such as *E. coli*. Once injected into the cell, the foreign DNA circularizes under the influence of the cos sticky ends. In this manner large segments of foreign DNA can be introduced and expressed in recombinant host cells.

Isolation and Cloning of Genes Encoding Glycerol Dehydratase (dhaB) and 1,3-propanediol Oxidoreductase (dhaT)

Identification and isolation of dhaB and dhaT were done essentially as described in U.S. Pat. No. 5,686,276 and those methods are hereby incorporated by reference. Cosmid vectors and cosmid transformation methods were used within the context of the present invention to clone large segments of genomic DNA from bacterial genera known to possess genes capable of processing glycerol to 1,3-propanediol. Two 1,3-propanediol positive transformants were analyzed and DNA sequencing revealed extensive homology to the glycerol dehydratase gene (dhaB) from *C. freundii*, demonstrating that these transformants contained DNA encoding the glycerol dehydratase gene. dhaB and dhaT were isolated and cloned into appropriate expression cassettes for co-expression in recombinant hosts with genes encoding $B_{12}$ coenzyme synthesis.

Although the instant invention uses the isolated genes from within a *Klebsiella* cosmid, alternate sources of dehydratase genes include, but are not limited to, *Citrobacter*, *Clostridia*, *Enterobacter*, and *Salmonella*.

$B_{12}$ Coenzyme Genes

Rational for $B_{12}$ Coenzyme Genes

Adenosylcobalamin (coenzyme $B_12$) is an essential cofactor for glycerol dehydratase activity. The coenzyme is the most complex non-polymeric natural product known, and its synthesis in vivo is directed using the products of about 20–30 genes. Synthesis of coenzyme $B_{12}$ is found in prokaryotes, some of which are able to synthesize the compound de novo, while others can perform partial reactions. *E. coli*, for example, cannot fabricate the corrin ring structure, but is able to catalyze the conversion of cobinamide to corrinoid and can introduce the 5'-deoxyadenosyl group.

Eukaryotes are unable to synthesize coenzyme $B_{12}$ de novo and instead transport vitamin $B_{12}$ and other coenzyme $B_{12}$ precursors from the extracellular milieu with subsequent conversion of the compound to its functional form of the compound by cellular enzymes. Three enzyme activities have been described for this series of reactions: 1) aquacobalamin reductase (EC 1.6.99.8) reduces Co(III) to Co(II); 2) cob(II)alamin reductase (EC 1.6.99.9) reduces Co(II) to Co(I); and 3) cob(I)alamin adenosyltransferase (EC 2.5.1.17) transfers a 5'-deoxyadenosine moiety from ATP to the reduced corrinoid. This last enzyme activity is the best characterized of the three and is encoded by cobA in *S. typhimurium*, btuR in *E. coli* and cobO in *P. denitrificans*. These three cob(I)alamin adenosyltransferase genes have been cloned and sequenced. Cob(I)alamin adenosyltransferase activity has been detected in human fibroblasts and in isolated rat mitochondria (Fenton et al., *Biochem. Biophys. Res. Commun.* 98, 283–9, (1981)). The two enzymes involved in cobalt reduction are poorly characterized and gene sequences are not available. There are reports of an aquacobalamin reductase from *Euglena gracilis* (Watanabe et al., *Arch. Biochem. Biophys.* 305, 421–7, (1993)) and a microsomal cob(III)alamin reductase is present in the microsomal and mitochondrial inner membrane fractions from rat fibroblasts (Pezacka, *Biochim. Biophys. Acta,* 1157, 167–77, (1993)).

Supplementing culture media with vitamin $B_{12}$ may satisfy the need to produce coenzyme $B_{12}$ for glycerol dehydratase activity in many microorganisms, but in some cases additional catalytic activities may have to be added or increased in vivo particularly when high levels of 1,3-propanediol are desired. Enhanced synthesis of coenzyme $B_{12}$ in eukaryotes may be particularly desirable. Given the published sequences for genes encoding cob(I)alamin adenosyltransferase, the cloning and expression of this gene could be accomplished by one skilled in the art. For example, it is contemplated that yeast, such as *Saccharomyces*, could be constructed so as to contain genes encoding cob(I)alamin adenosyltransferase in addition to the genes necessary to effect conversion of a carbon substrate such as glucose to 1,3-propanediol. Cloning and expression of the genes for cobalt reduction requires a different approach. This could be based on a selection in *E. coli* for growth on ethanolamine as sole C or $N_2$ source. In the presence of coenzyme $B_{12}$, ethanolamine ammonia-lyase enables growth of cells in the absence of other C or $N_2$ sources. If *E. coli* cells contain a cloned gene for cob(I)alamin adenosyltransferase and random cloned DNA from another organism, growth on ethanolamine in the presence of aquacobalamin should be enhanced and selected for if the random cloned DNA encodes cobalt reduction properties to facilitate adenosylation of aquacobalamin.

Another approach to identifying and cloning the gene(s) for cobalt reduction is based on coenzyme $B_{12}$ repression of btuB expression. When *E. coli* is grown in the presence of coenzyme $B_{12}$ the expression of btuB is reduced, and if a btuB::lacZ fusion is constructed this repression can be observed as a reduction in β-galactosidase activity. Vitamin $B_{12}$ will also repress expression of btuB::lacZ once it has been adenosylated, but factors that prevent conversion to coenzyme $B_{12}$, such as defects in cobalt reduction or adenosylation, lead to constitutive expression of btuB::lacZ. To identify cobalt reduction genes requires the initial selection or identification of Lac+ cells from a btuB::lacZ strain that has been subjected to mutagenesis, followed by positive selection for growth on lactose, or by identifying Lac+ colonies on indicator plates. False positives due to btuR mutations could be minimized by having btuR present on a plasmid. A strain defective in cobalt reduction can be transformed with cloned DNA from the same or another species, and cloned cobalt reduction genes identified because of a Lac− phenotype resulting from coenzyme $B_{12}$ repression of btuR::lacZ expression.

Isolation of Genes Encoding Cob(I)alamin Adenosyltransferase

The genes encoding cob(I)alamin adenosyltransferase were cloned from two species of bacteria, btuR from *E. coli* strain DH5α(deoR endA1 gyrA96 hsdR17(rk− mk+) recA1 relA1 supE44 thi-1 Δ(lacZYA-argFV169)) and cobA from *S. typhimurium* strain ATCC 23564. Primers were designed using the published sequence of btuR (Lundrigan and Kadner, *J. Bact.* 171, 154–161 (1989)) such that PCR-amplification of the gene from *E. coli* could be achieved to give the complete coding sequence flanked by HindIII and BamHI sites to the 5' end, and a PstI site to the 3' end. A ribosome binding site was present between the HindIII and BamHI sites at the 5' end to ensure adequate translation. The PCR product was cloned into the SrfI site of pCR-Script to give plasmid pAH61. A correctly constructed clone was confirmed by DNA analysis and by functional expression to complement an *E. coli* btuR mutant strain for 1,3-propanediol production. Primers were also designed for the *S. typhimurium* cobA gene using published sequence (Suh and Escalante-Semerena, *Gene* 129, 93–97 (1993)) such that PCR-amplification of the gene could be achieved to give the complete coding sequence flanked by HindIII and BamHI sites to the 5' end, and a PstI site to the 3' end. A ribosome binding site was present between the HindIII and BamHI sites at the 5' end to ensure adequate translation. The PCR product was cloned into the SrfI site of pCR-Script to give plasmid pAH63. A correctly constructed clone was confirmed by DNA analysis and by functional expression to complement an *E. coli* btuR mutant strain for 1,3-propanediol production.

Isolation of the Cob(II)alamin Reductase Gene

Cob(II)alamin reductase has been purified 6300-fold to homogeneity from *P. denitrificans* strain SC510 (Blanche et al., *J. Bact.* 174, 7452–7454 (1992)). The N-terminal amino acid sequence was determined to be Met Glu Lys Thr Arg Leu (SEQ ID NO: 26), from which one skilled in the art can design a suitable population of primers that encompasses all possible nucleotide variations that encode this peptide [ATG GAR AAR ACS CGI CTI, where R=A+G; S=C+G; [I]=Inosine] (SEQ ID NO:8). The pool of primers thus obtained is used for PCR-amplification of the gene for cob(II)alamin reductase using either of two techniques. In one approach, chromosomal DNA from *P. denitrificans* is subjected to PCR with the pool of primers encoding Met Glu Lys Thr Arg Leu (SEQ ID NO: 26), together with random primers to effect second strand synthesis. PCR products are cloned into a plasmid, such as pCR-Script, and the cloned fragments screened by DNA sequence analysis. Another approach is to first clone DNA from *P. denitrificans* into a plasmid such as pCR-Script, followed by PCR amplification using the pool of primers encoding Met Glu Lys Thr Arg Leu (SEQ ID NO:26) for first strand synthesis. Second strand synthesis is accomplished by using a primer a sequence derived from the known plasmid sequence. The isolated complete or partial sequence for cob(II)alamin reductase from *P. denitrificans* is used as a probe to identify and clone similar genes from other species that encode this enzyme.

Development of an appropriate selection strategy based on complementation allows identification and isolation of the gene for cob(II)alamin reductase. Lundrigan and Kadner (*J. Bact* 171, 154–161 (1989)) describe how btuR (adenosyltransferase) mutants influence btuB (outer-membrane $B_{12}$ binding protein) gene regulation. The btuR mutants are identified because they do not repress btuB expression. This is done by first making a gene fusion between btuB and lacZ. Growth of these cells in the absence of vitamin $B_{12}$ or coenzyme $B_{12}$ leads to constitutive expression of btuB::lacZ (so that $B_{12}$ receptors are present on the cell surface) to give a Lac$^{30}$ phenotype. In wild type cells vitamin $B_{12}$ undergoes cobalt reduction, and is then converted to coenzyme $B_{12}$ by cob(I)alamin adenosyltransferase, and the resulting coenzyme $B_{12}$ causes repression of btuB::lacZ to give a Lac− phenotype. In btuR mutants the vitamin $B_{12}$ is not converted to coenzyme $B_{12}$, repression of btuB::lacZ does not occur and a Lac+ phenotype is observed on media containing vitamin $B_{12}$. Therefore, to isolate btuR mutants requires selection or identification of Lac+ cells from a btuB::lacZ strain in the presence of vitamin $B_{12}$. Since the cob(II) alamin reductase, like BtuR, functions during the conversion of vitamin $B_{12}$ to coenzyme $B_{12}$, the same requirement for growth on media containing lactose and vitamin $B_{12}$ of a btuB::lacZ strain enables a positive selection for mutations in cob(II)alamin reductase. Alternatively, such mutations are observed as Lac+ colonies on indicator plates. False positives due to btuR mutations are minimized by having btuR present on a multicopy plasmid. Isolation of mutations in the gene for cob(II)alamin reductase is achieved by chemical mutagenesis, UV light or by the use of transposons such as Tn5 or Tn10. Strains with mutations in cob(II)alamin reductase are complemented using a cloned genomic library to give a Lac− phenotype on Lac indicator plates, leading to identification of the specific gene. In addition to using a library of cloned DNA to identify a cob(II)alamin reductase through complementation, defined fragments of cloned DNA encoding reductases are used to assess complementation. A fragment of chromosomal DNA from *E. coli* (bearing the yciK gene (GenBank C006550) (SEQ ID NO:9) encoding a dehydrogenase/reductase or a related sequence from other prokaryotes) is tested in the complementation assay for a Lac− phenotype resulting from reduction and adenosylation of vitamin $B_{12}$ to form coenzyme $B_{12}$, which in turn will repress expression of btuB::lacZ. yciK, located immediately upstream of btuR, is transcribed in the same direction, and the termination codon (UGA) of yciK overlaps with the initiation codon (AUG) of btuR in the genomic sequence ATGA. This sequential arrangement of termination and initiation codons is a characteristic of genes that are translationally coupled and co-regulated (Gatenby et al., *Proc. Natl. Acad. Sci. USA* 86, 4066–4070 (1989)). *E. coli* yciK is a particularly preferred gene to enable cobalt reduction during the synthesis of coenzyme $B_{12}$.

The skilled artisan will appreciate that utility of the dehydrogenase/reductase activity encoded by yciK will not be limited to this specific gene or enzyme but will include homologues of the gene or enzyme including genes and enzymes that are substantially similar to the gene or enzyme and those genes having about 80% identity to the gene, where those having 90% identity re preferred, and where that having about 95% identity are most preferred.

In addition to selections based on a Lac phenotype, it is possible to use *E. coli* strains which carry a defective metE gene that encodes a cobalamin-independent methionine synthase, but which retain a functional metH gene encoding a cobalamin-dependent methionine synthase. An example of such a strain is CAG18491(F$^-$, λ$^-$, rph-1, metE3079::Tn10), a methionine auxotroph unless vitamin or coenzyme B$_{12}$ is added to the media. Mutagenesis of CAG18491 and growth on minimal media containing coenzyme B$_{12}$, followed by colony testing on minimal media containing vitamin B$_{12}$, allows identification of cells that have lost the ability to convert vitamin to coenzyme B$_{12}$, but which can still use coenzyme B$_{12}$ during the synthesis of methionine by the MetH methionine synthase. The cells identified in this screen are defective in one of the two cobalt reduction steps, or in adenosylation of vitamin B$_{12}$. Introduction of a cloned btuR plasmid into cells that are methionine auxotrophs on vitamin B$_{12}$ but are prototrophs on coenzyme B$_{12}$ will identify cells that remain Met$^-$ on vitamin B$_{12}$, even though btuR is present. Alternatively, a plasmid bearing btuR is added to the metE strain prior to mutagenesis and selection. Cells that are defective in one or both of the two cobalt reduction steps can be used to screen a genomic library for clones that restore prototrophic growth on minimal media with vitamin B$_{12}$. To preclude cloning of the metE gene in this selection it is important to prepare the genomic library from a strain that has a defective metE gene. Plasmids obtained from this selection will encode an enzyme capable of reducing cobalt. Assaying for cob(II)alamine reductase confirms this property.

Isolation of the Aquacobalamin Reductase Gene

Aquacobalamin reductase is purified from, but is not limited to, *Pseudomonas, Escherichia, Salmonella, Klebsiella* or *Citrobacter*, as described by Watanabe and Nakono (*Methods Enzymol.* 281, 289–305 (1997)) or with variations thereof. An enzyme assay is used that measures the decrease in absorbance of aquacobalamin at 525 nm (Watanabe et al., *J. Nutr.* 126, 2947–2951 (1996)). The N-terminal amino acid sequence of the protein is determined, from which one skilled in the art can design a collection of primers that includes all possible nucleotide variations that encode the N-terminal peptide. The pool of primers thus obtained is used for PCR-amplification of the gene for aquacobalamin reductase using either of two techniques. In one approach, chromosomal DNA is subjected to PCR with the pool of primers encoding the N-terminal peptide, together with random primers to effect second strand synthesis. PCR products are cloned into a plasmid, such as pCR-Script, and the cloned fragments screened by DNA sequence analysis. Another approach is to first clone chromosomal DNA into a plasmid such as pCR-Script, followed by PCR amplification using the pool of primers encoding the N-terminal peptide for first strand synthesis. Second strand synthesis is accomplished by using as a primer a sequence derived from the known plasmid sequence. The isolated complete or partial sequence for aquacobalamin reductase is used as a probe to identify and clone similar genes from other species that encode this enzyme.

Identification and isolation of the gene for aquacobalamin reductase arises from an appropriate selection strategy based on complementation. Lundrigan and Kadner (*J. Bact* 171, 154–161 (1989)) describe how btuR (adenosyltransferase) mutants influence btuB (outer-membrane B$_{12}$ binding protein) gene regulation. The btuR mutants are identified because they do not repress btuB expression. This is done by first making a gene fusion between btuB and lacZ. Growth of these cells in the absence of vitamin B$_{12}$ or coenzyme B$_{12}$ leads to constitutive expression of btuB::lacZ (so that B$_{12}$ receptors are present on the cell surface) to give a Lac$^+$ phenotype. In wild type cells vitamin B$_{12}$ undergoes cobalt reduction, and is then converted to coenzyme B$_{12}$ by cob(I) alamin adenosyltransferase. The resulting coenzyme B$_{12}$ causes repression of btuB::lacZ to give a Lac$^-$ phenotype. In btuR mutants the vitamin B$_{12}$ is not converted to coenzyme B$_{12}$, repression of btuB::lacZ does not occur, and a Lac$^+$ phenotype is observed on media containing vitamin B$_{12}$. Therefore, to isolate btuR mutants requires selection or identification of Lac$^+$ cells from a btuB::lacZ strain in the presence of vitamin B$_{12}$. Since the aquacobalamin reductase, like BtuR, functions during the conversion of vitamin B$_{12}$ to coenzyme B$_{12}$, the same requirement for growth on media containing lactose and vitamin B$_{12}$ of a btuB::lacZ strain enables a positive selection for mutations in aquacobalamin reductase. Alternatively, such mutations are observed as Lac$^+$ colonies on indicator plates. False positives due to btuR mutations are minimized by having btuR present on a multicopy plasmid. Isolation of mutations in the gene for aquacobalamin reductase is achieved by chemical mutagenesis, UV light or by the use of transposons such as Tn5 or Tn10. Strains with mutations in aquacobalamin reductase are complemented using a cloned genomic library to give Lac$^-$ phenotype on Lac indicator plates, leading to identification of the specific gene. In addition to such complementation using a library of cloned DNA to identify an aquacobalamin reductase, defined fragments of cloned DNA encoding a reductase are used to assess complementation In addition to selections based on a Lac phenotype, it is possible to use *E. coli* strains which carry a defective metE gene that encodes a cobalamin-independent methionine synthase, but which retain a functional metH gene encoding a cobalamin-dependent methionine synthase. The procedure follows that described above for the isolation of Cob(II) alamin reductase gene. Plasmids obtained from this selection will encode an enzyme capable of reducing cobalt. Assaying for aquacobalamin reductase confirms this property.

Host Cells

Suitable host cells for the recombinant production 1,3-propanediol by the coexpression of a gene encoding a dehydratase enzyme and the genes encoding cob(I)alamin adenosyltransferase, aquacobalamin reductase and cob(II) alamin reductase may be either prokaryotic or eukaryotic and will be limited only by their ability to express active enzymes. Preferred hosts will be those typically useful for production of 1,3-propanediol or glycerol such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces* and *Pseudomonas*. Most preferred in the present invention are *E. coli, Klebsiella* species and *Saccharomyces* species.

*E. coli* and *Klebsiella* species are particularly preferred hosts. Strains of *Klebsiella pneumoniae* are known to produce 1,3-propanediol when grown on glycerol as the sole carbon. It is contemplated that *Klebsiella* can be genetically altered to produce 1,3-propanediol from monosaccharides, oligosaccharides, polysaccharides, or one-carbon substrates.

Vectors and Expression Cassettes

The present invention provides a variety of vectors and transformation and expression cassettes suitable for the cloning, transformation and expression of genes encoding a suitable dehydratase and of genes effecting the conversion of coenzyme $B_{12}$ precursors to coenzyme $B_{12}$ into a suitable host cell. Suitable vectors will be those which are compatible with the bacterium used as a host cell. Suitable vectors can be derived, for example, from a bacteria, a virus (such as bacteriophage T7 or a M-13 derived phage), a cosmid, a yeast or a plant. Protocols for obtaining and using such vectors are known to those in the art. (Sambrook et al., Molecular Cloning: A Laboratory Manual—volumes 1,2,3 (Cold Spring Harbor Laboratory, Cold Spring Harbor, N.Y., (1989)).

Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions or promoters, useful to drive expression of the relevant genes of the present invention in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Transformation of Suitable Hosts and Expression of Genes for the Production of 1,3-propanediol Once suitable cassettes are constructed they are used to transform appropriate host cells. Introducing into the host cell the cassette containing the genes encoding cob(I)alamin adenosyltransferase, aquacobalamin reductase, cob(II) alamin reductase, glycerol dehydratase (dhaB), and 1,3-propanediol oxidoreductase (dhaT) (either separately or together) may be accomplished by known procedures including transformation (e.g., using calcium-permeabilized cells, electroporation) or by transfection using a recombinant phage virus. (Sambrook et al., supra.)

In the present invention, *E. coli* FM5 containing the genes encoding glycerol dehydratase (dhaB), 1,3-propanediol oxidoreductase (dhaT), aquacobalamin reductase, cob(II) alamin reductase, and cob(I)alamin adenosyltransferase is used to convert vitamin $B_{12}$ supplied in the media to coenzyme $B_{12}$ to enable glycerol dehydratase to function.

Media and Carbon Substrates

Fermentation media in the present invention must contain suitable carbon substrates. Suitable substrates may include but are not limited to glycerol, dihydroxyacetone, monosaccharides such as glucose and fructose, oligosaccharides such as lactose or sucrose, polysaccharides (such as starch or cellulose), or mixtures thereof, and unpurified mixtures from renewable feedstocks (such as cheese whey permeate, cornsteep liquor, sugar beet molasses, and barley malt). Additionally, the carbon substrate may also be one-carbon substrates (such as carbon dioxide or methanol) for which metabolic conversion into key biochemical intermediates has been demonstrated.

Glycerol production from single carbon sources (e.g., methanol, formaldehyde, or formate) has been reported in methylotrophic yeasts (Yamada et al., *Agric. Biol. Chem.*, 53(2) 541–543, (1989)) and in bacteria (Hunter et al., *Biochemistry*, 24, 4148–4155, (1985)). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153(5), 485–9 (1990)). Accordingly, the source of carbon utilized in the present invention may encompass a wide variety of carbon-containing substrates and will only be limited by the requirements of the host organism.

All of the above mentioned carbon substrates and mixtures thereof are expected to be suitable in the present invention. However, preferred carbon substrates are glycerol, dihydroxyacetone, monosaccharides, oligosaccharides, polysaccharides, and one-carbon substrates. More preferred are sugars such as glucose, fructose, sucrose and single carbon substrates such as methanol and carbon dioxide. Most preferred is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production. Particular attention is given to Co(II) salts and/or vitamin $B_{12}$ or other alternate coenzyme $B_{12}$ precursors. For example, *E. coli* and eukaryotes are unable to synthesize coenzyme $B_{12}$ de novo but are able to utilize coenzyme $B_{12}$ precursors. Preferred coenzyme $B_{12}$ precursors are vitamin $B_{12}$ and hydroxocobalamin. It is desirable that the amount of coenzyme $B_{12}$ inside the host cell be approximately equal in molar concentration to the amount of dehydratase enzyme.

Culture Conditions

Typically, cells are grown at 30° C. in appropriate media. Preferred growth media in the present invention are common commercially prepared media such as Luria Bertani (LB) broth, Sabouraud Dextrose (SD) broth or Yeast Malt Extract (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 3':5'-monophosphate, may also be incorporated into the reaction media. Similarly, the use of agents known to modulate enzymatic activities (e.g., sulphites, bisulphites and alkalis) that lead to enhancement of glycerol production may be used in conjunction with or as an alternative to genetic manipulations.

Suitable pH ranges for the fermentation are between pH 5.0 to pH 9.0, where pH 6.0 to pH 8.0 is preferred as the range for the initial condition.

Reactions may be performed under aerobic or anaerobic conditions where anaerobic or microaerobic conditions are preferred.

Fermentations

The present invention may be practiced using either batch, fed-batch, or continuous processes and any known mode of fermentation would be suitable. Additionally, cells may be immobilized on a substrate as whole cell catalysts and subjected to fermentation conditions for 1,3-propanediol production.

The present process is exemplified herein as a batch method of fermentation. A classical batch fermentation is a closed system where the composition of the media is set at the beginning of the fermentation and not artificially altered during the fermentation. Thus, at the beginning of the fermentation the media is inoculated with the desired organism or organisms and fermentation is permitted to occur adding nothing to the system. Typically, however, a batch fermentation is "batch" with respect to the addition of the carbon source and attempts are often made at controlling factors such as pH and oxygen concentration. The metabolite and biomass compositions of the batch system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch fermentation system which is also suitable in the present invention. In this variation of a typical batch system, the substrate is added in increments as the fermentation progresses. Fed-Batch systems are useful when catabolite repression is apt to inhibit the metabolism of the cells and where it is desirable to have limited amounts of substrate in the media. Measuring the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, infra.

The method also is expected to be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology. A variety of methods are detailed by Brock, infra.

Identification and Purification of 1,3-Propanediol:

Methods for the purification of 1,3-propanediol from fermentation media are known in the art. For example, propanediols can be obtained from cell media by subjecting the reaction mixture to extraction with an organic solvent, distillation, and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. The preferred method is analysis of the fermentation media on an analytical ion exchange column using a mobile phase of 0.01 N sulfuric acid in an isocratic fashion.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures for phosphorylations, ligations and transformations are well known in the art. Techniques suitable for use in the following examples may be found in Sambrook, J. et al., *Molecular Cloning: A Laboratory Manual*, Second Edition, Cold Spring Harbor Laboratory Press, Cold Spring Harbor, N.Y. (1989).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Cells

E. coli strain DH5α was purchased from Gibco/BRL, Gaithersburg, Md. K. pneumoniae strain ATCC 25955, K. oxytoca strain ATCC 8724, and S. typhimurium strain ATCC 23564 were purchased from the American Type Culture Collection (ATCC), Rockville, Md. E. coli strain FM5 (ATCC 53911), Amgen U.S. Pat. No. 5,494,816, is available from ATCC E. coli strain RK6726 (Lundrigan et al., Mol. Gen. Genet. 206, 401–407 (1987)) was a gift from R. Kadner. E. coli strain CAG18491 was purchased from the E. coli Genetic Stock Center, Yale University, New Haven, Conn. K. oxytoca strain M5a1 was purchased from National Collections of Industrial and Marine Bacteria, Ltd., Aberdeen, Scotland (NCIMB #12204). S. cerevisiae strain YPH499 (ura3-52 lys2-801 ade2-101 trp1-del63 his3-del200 leu2-del1) was purchased from Stratagene, La Jolla, Calif. P. pastoris strain GTS 115 (his4) was obtained from Phillips Petroleum, Bartlesville, Okla. A. niger strain FS1 is a proprietary strain from Genencor International, Inc.

Isolation and Identification 1,3-propanediol

The conversion of glycerol to 1,3-propanediol was monitored by HPLC. Analyses were performed using standard techniques and materials available to one skilled in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N $H_2SO_4$ as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated were compared to that of authentic 1,3-propanediol (m/e: 57, 58).

An alternative method for GC/MS involved derivatization of the sample. To 1.0 mL of sample (e.g., culture supernatant) was added 30 uL of concentrated (70% v/v) perchloric acid. After mixing, the sample was frozen and lyophilized. A 1:1 mixture of bis(trimethylsilyl)trifluoroacetamide:pyridine (300 uL) was added to the lyophilized material, mixed vigorously and placed at 65° C. for one h. The sample was clarified of insoluble material by centrifugation. The resulting liquid partitioned into two phases, the upper of which was used for analysis. The sample was chromatographed on a DB-5 column (48 m, 0.25 mm I.D., 0.25 um film thickness; from J&W Scientific) and the retention time and mass spectrum of the 1,3-propanediol derivative obtained from culture supernatants were compared to that obtained from authentic standards. The mass spectrum of TMS-derivatized 1,3-propanediol contains the characteristic ions of 205, 177, 130 and 115 AMU.

Assay for Cob(I)alamin Adenosyltransferase and Cob(II)alamin Reductase Activity.

Cob(I)alamin adenosyltransferase may be assayed as described by S.-J. Suh and J. C. Escalante-Semerena, J. Bacteriol. 177, 921–925 (1995) or L. Debussche et al., J. Bacteriol. 173, 6300–6302 (1991). Alternatively, cob(I) alamin adenosyltransferase may be determine by an in vivo assay as described in Example 1.

Cob(II)alamin reductase may be assayed as described by L. Debussche et al., J. Bacteriol. 174, 7452–7454 (1992).

Isolation and Cloning of Genes Encoding Glycerol Dehydratase (dhaB) and 1,3-propanediol Oxidoreductase (dhaT)

Identification and isolation of dhaB and dhaT were done essentially as described in U.S. Pat. No. 5,686,276 and those methods are hereby incorporated by reference. Cosmid vectors and cosmid transformation methods were used to clone large segments of genomic DNA from bacterial genera known to possess genes capable of processing glycerol to 1,3-propanediol. Specifically, genomic DNA from K. pneumoniae ATCC 25955 was isolated by methods well known in the art and digested with the restriction enzyme Sau3A for insertion into a cosmid vector Supercos 1 and packaged using GigapackII packaging extracts. Following construction of the vector E. coli XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene (dhaB) from C. freundii, demonstrating that these transformants contained DNA encoding the glycerol dehydratase gene.

A 12.1 kb EcoRI-SalI fragment from pKP1, subcloned into pIBI31 (IBI Biosystem, New Haven, Conn.), was sequenced and termed pHK28-26 (SEQ ID NO:10). Sequencing revealed the loci of the relevant open reading frames of the dha operon encoding glycerol dehydratase and genes necessary for regulation. Referring to SEQ ID NO:10, a fragment of the open reading frame for dhaK (encoding dihydroxyacetone kinase) is found at bases 1–399; the open reading frame dhaD (encoding glycerol dehydrogenase) is found at bases 983–2107; the open reading frame dhaR (encoding the repressor) is found at bases 2209–4134; the open reading frame dhaT (encoding 1,3-propanediol oxidoreductase) is found at bases 5017–6180; the open reading frame dhaB1 (encoding the alpha subunit glycerol dehydratase) is found at bases 7044–8711; the open reading frame dhaB2 (encoding the beta subunit glycerol dehydratase) is found at bases 8724–9308; the open reading frame dhaB3 (encoding the gamma subunit glycerol dehydratase is found at bases 9311–9736; and the open reading frame dhaBX (encoding a protein of unknown function) is found at bases 9749–11572. Additionally, the open reading frame orfY (encoding a protein of unknown function) is found at bases 6202–6630; the open reading frame orfX (encoding a protein of unknown function) is found at bases 4643–49, and the open reading frame orfW (encoding a protein of unknown function) is found at bases 4112–4642.

Construction of General Purpose Expression Plasmids for Use in Transformation of *Escherichia coli*

Construction of Expression Vector pTacIQ

The *E. coli* expression vector pTacIQ was prepared by inserting lacIq gene (Farabaugh, P. J., *Nature* 274 (5673) 765–769, (1978)) and tac promoter (Amann et al., *Gene* 25, 167–178 (1983)) into the restriction endonuclease site EcoRI of pBR322 (Sutcliffe, *Cold Spring Harb. Symp. Quant. Biol.* 43, 77–90 (1979)). A multiple cloning site and terminator sequence (SEQ ID NO:11) replaces the pBR322 sequence from EcoRI to SphI.

Subcloning the Glycerol Dehydratase Genes (dhaB1, 2,3, X)

The open reading frame for the dhaB3 gene was amplified from pHK 28-26 by PCR using primers (SEQ ID NO:12 and SEQ ID NO:13) incorporating an EcoRI site at the 5' end and a XbaI site at the 3' end. The product was subcloned into pLitmus29 (New England Biolab, Inc., Beverly, Mass.) to generate the plasmid pDHAB3 containing dhaB3.

The region containing the entire coding region for dhaB1, dhaB2, dhaB3 and dhaBX of the dhaB operon from pHK28-26 was cloned into pBluescriptIIKS+ (Stratagene, La Jolla, Calif.) using the restriction enzymes KpnI and EcoRI to create the plasmid pM7.

The dhaBX gene was removed by digesting plasmid pM7 with ApaI and XbaI, purifying the 5.9 kb fragment and ligating it with the 325-bp ApaI-XbaI fragment from plasmid pDHAB3 to create pM11 containing dhaB1, dhaB2 and dhaB3.

The open reading frame for the dhaB1 gene was amplified from pHK28-26 by PCR using primers (SEQ ID NO:14 and SEQ ID NO:15) incorporating a HindIII site and a consensus ribosome binding site at the 5' end and a XbaI site at the 3' end. The product was subcloned into pLitmus28 (New England Biolab, Inc.) to generate the plasmid pDT1 containing dhaB1.

A NotI-XbaI fragment from pM11 containing part of the dhaB1 gene, the dhaB2 gene and the dhaB3 gene was inserted into pDT1 to create the dhaB expression plasmid, pDT2. The HindIII-XbaI fragment containing the dhaB(1, 2,3) genes from pDT2 was inserted into pTacIQ to create pDT3.

Subcloning the 1.3-propanediol Dehydrogenase Gene (dhaT)

The KpnI-SacI fragment of pHK28-26, containing the 1,3-propanediol dehydrogenase (dhaT) gene, was subcloned into pBluescriptII KS+ creating plasmid pAH1. The dhaT gene was amplified by PCR from pAH1 as template DNA and synthetic primers (SEQ ID NO:16 with SEQ ID NO:17) incorporating an XbaI site at the 5' end and a BamHI site at the 3' end. The product was subcloned into pCR-Script (Stratagene) at the SrfI site to generate the plasmids pAH4 and pAH5 containing dhaT. The plasmid pAH4 contains the dhaT gene in the right orientation for expression from the lac promoter in pCR-Script and pAH5 contains dhaT gene in the opposite orientation. The XbaI-BamHI fragment from pAH4 containing the dhaT gene was inserted into pTacIQ to generate plasmid pAH8. The HindIII-BamHI fragment from pAH8 containing the RBS and dhaT gene was inserted into pBluescriptIIKS+ to create pAH11.

Construction of an Expression Cassette for dhaT and dhaB (1,2,3)

An expression cassette for dhaT and dhaB(1,2,3) was assembled from the individual dhaB(1,2,3) and dhaT subclones described previously using standard molecular biology methods. A SpeI-SacI fragment containing the dhaB(1, 2,3) genes from pDT3 was inserted into pAH11 at the SpeI-SacI sites to create pAH24. A SalI-XbaI linker (SEQ ID NO:18 and SEQ ID NO:19) was inserted into pAH5 which was digested with the restriction enzymes SalI-XbaI to create pDT16. The linker destroys the XbaI site. The 1 kb SalI-MluI fragment from pDT16 was then inserted into pAH24 replacing the existing SalI-MluI fragment to create pDT18. pDT21 was constructed by inserting the SalI-NotI fragment from pDT18 and the NotI-XbaI fragment from pM7 into pCL1920 (SEQ ID NO:20). The glucose isomerase promoter sequence from *Streptomyces* (SEQ ID NO:21) was cloned by PCR and inserted into EcoRI-HinDIII sites of pLitmus28 to construct pDT5. pCL1925 was constructed by inserting EcoRI-PvuII fragment of pDT5 into the EcoRI-PvuI site of pCL1920. pDT24 was constructed by cloning the HinDIII-MluII fragment of pDT21 and the MluI-XbaI fragment of pDT21 into the HinDIII-XbaI sites of pCL1925.

Example 1 btuR and cobA: Gene Isolation, Plasmid Construction and Activity

The *E. coli* DH5α (deoR end1 gyrA96 hsdR17(rk– mk+) recA1 relA1 supE44 thi-1 Δ(lacZYA-argFV169)) strain used for isolation of the cob(I)alamin adenosyltransferase (btuR) gene was purchased from Gibco BRL (Gaithersburg, Md.). btuR was amplified from chromosomal DNA by PCR using synthetic primers (SEQ ID NO:22 with SEQ ID NO:23) incorporating a ribosome binding site flanked by HindIII and BamHI sites at the 5' end and a PstI site at the 3' end. The product was subcloned into pCR-Script (Stratagene, Madison, Wis.) at the SrfI site to generate the plasmid pAH61 containing btuR in the correct orientation for expression from the lac promoter.

The activity of pAH61 was demonstrated by restoring 1,3-propanediol production in an *E. coli*, btuR minus background (RK6726, Lundrigan et al., Mol. Gen. Genet. 206, 401–407 (1987)). *E. coli* strains RK6726/pDT24 and RK6726/pDT24/pAH61 were grown in erlenmeyer flasks containing medium at one fifth the volume of flask capacity. The plasmid pDT24 contains the genes encoding glycerol dehydratase and 1,3-propanediol oxidoreductase). Medium, titrated to pH 6.8 with HCl, contained 0.2 M $K_2HPO_4$, 2.0 g/L citric acid, 2.0 g/L $MgSO_4.7H_2O$, 1.2 mL 98% $H_2SO_4$, 0.30 g/L ferric ammonium citrate, 0.20 g/L $CaCl_2.2H_2O$, 5 g/L yeast extract, 15 g/L D-glucose, 60 g/L glycerol, 5 mL per liter of Modified Balch/Es Trace-Element Solution (Cote, R. J., and Ghema, R. L. In *Methods for General and Molecular Bacteriology*; Gerhardt, P. et al., Eds; American Society for Microbiology: Washington, D.C., 1994; p. 158), and 50 mg/L vitamin $B_{12}$. In addition, 50 ug/mL spectinomycin and 100 ug/mL carbencillin were used to maintain the plasmids pDT24 and pAH61, respectively. The shake flasks were incubated at 33° C. with vigorous shaking. After 48 hours, RK6726/pDT24/pAH61 ($OD_{600}$=9.8 AU) produced 4.0 g/L 1,3-propanediol. In the control experiment with RK6726/pDT24 (OD$_{600}$=10.1 AU), 1,3-propanediol was not detected.

The *S. typhimurium* strain (ATCC 23564) used for isolation of the cob(I)alamin adenosyltransferase (cobA) gene was purchased from the American Type Culture Collection (Rockville, Md.). cobA was amplified from chromosomal DNA by PCR using synthetic primers (SEQ ID NO:24 with SEQ ID NO:25) incorporating a ribosome binding site flanked by HindIII and BamHI sites at the 5' end and a PstI site at the 3' end. The product was subcloned into pCR-Script (Stratagene, Madison, Wis.) at the SrfI site to generate the plasmid pAH63 containing cobA in the correct orientation for expression from the lac promoter. The activity of pAH63 was demonstrated as described for pAH61.

Example 2

Cob(II)alamin Reductase: Gene Isolation and Plasmid Construction Media

Synthetic S12 medium is used in the screening of bacterial transformants for the ability to grow in the absence of methionine in the presence of either vitamin B$_{12}$ or coenzyme B$_{12}$. S12 medium contains: 10 mM ammonium sulfate, 50 mM potassium phosphate buffer, pH 7.0, 2 mM MgCl$_2$, 0.7 mM CaCl$_2$, 50 uM MnCl$_2$, 1 uM FeCl$_3$, 1 uM ZnCl, 1.7 uM CuSO$_4$, 2.5 uM CoCl$_2$, 2.4 uM Na$_2$MoO$_4$, and 2 uM thiamine hydrochloride. S12 medium is supplemented with 0.2% D-glucose, 2 mg/L uracil, and 400 ug/L vitamin B$_{12}$ or coenzyme B$_{12}$.

Selection for a Cob(II)alamin Reductase Defective Strain

*E. coli* strain CAG18491 (F$^-$, λ$^-$, rph-1, metE3079::Tn10) was purchased from the *E. coli* Genetic Stock Center, Yale University (New Haven, Conn.). All incubations are at 37° C. CAG18491 is grown in LB medium containing 10 mg/L tetracycline to an A$_{600}$ 0.3–0.4 AU, made competent by CaCl$_2$ treatment, and transformed with the btuR plasmid pAH61. Transformants are selected following overnight growth on LB plates containing 10 mg/L tetracycline and 50 mg/L ampicillin. A single transformant is grown in LB containing 10 mg/L tetracycline and 50 mg/L ampicillin to an A$_{600}$ 0.5–0.6 AU. 1 M MgSO$_4$ is added to give a final concentration of 10 mM, and bacteriophage λ::Tn5 is added to give an m.o.i. of 1. After 10 min to allow phage infection the culture is allowed to grow for an additional 60 min. Serial dilutions are plated on LB containing 10 mg/L tetracycline, 50 mg/L ampicillin and 25 mg/L kanamycin. Following overnight growth, several thousand colonies are pooled by scraping plates bearing well-separated colonies. The pool of cells is washed extensively by centrifugation and resuspension in S12 medium. Serial dilutions are plated on S12 plates containing coenzyme B$_{12}$ and incubated in the dark for 2 days. Colonies are replica-plated onto S12 plates containing vitamin B$_{12}$ and 0.1 mM isopropyl-β-D-galactopyranoside (IPTG) and incubated in the dark for 2 days. Colonies that fail to grow on vitamin B$_{12}$ but grow on coenzyme B$_{12}$ are enriched for mutations in the vitamin B$_{12}$ to coenzyme B$_{12}$ conversion, but will not be mutated in btuR because of the presence of the multicopy btuR plasmid pAH61, nor will they be defective in cobalamin transport or methionine synthesis because they grow on minimal media containing coenzyme B$_{12}$. Putative cobalt reductase mutants are assayed for the loss of cob(II)alamin reductase using the in vivo assay with cells treated with toluene and incubated with reduced hydroxycobalamin.

A characterized cob(II)alamin reductase mutant is used to select by complementation a gene that will restore growth on S12 plates containing vitamin B$_{12}$ and IPTG. Chromosomal DNA is isolated from CAG18491, or from other strains or species that are metE, and partially digested with the restriction enzyme Sau3A. The Sau3A fragments are ligated into the BamHI site of plasmid pACYC184 and transformed into the cob(II)alamin reductase minus strain. Plasmid pACYC184 (chlR) is compatible with pAH61 (ampR), and the presence of Tn5 (kanR) and Tn10 (tetR) are confirmed by resistance to the appropriate antibiotic. The transformed library-containing cells are plated on S12 plates containing vitamin B$_{12}$ and 0.1 mM IPTG and incubated in the dark for 2 days. Plasmids that restore growth of cells by complementation under these growth conditions are screened using the in vitro cob(II)alamin reductase assay to confirm the presence of the cloned gene.

Example 3

Host Construction

*E. coli* strain FM5 is co-transformed with the dha plasmid pDT24 (specR), the btuR plasmid pAH61 (ampR), and the cob(II)alamin reductase plasmid based on pACYC184 (chlR). Selection is on LB plates containing 50 mg/L spectinomycin, 50 mg/L ampicillin and 100 mg/L chloramphenicol. Colonies resistant to all three antibiotics are used for 1.3-propanediol production.

Example 4

Enhanced 1.3-propanediol Production

Growth of cells from Example 3 to give an improvement in 1,3-propanediol production is carried at 37° C. in shake-flask cultures (erlenmeyer flasks, liquid volume one tenth that of total volume).

*E. coli* strain FM5/pDT24 cotransformed with pAH61 and the cob(II)alamin reductase plasmid is grown in 250 mL flasks containing 25 mL of medium at 30° C. with shaking at 250 rpm. FM5/pDT24 (the parent strain) is grown in parallel as the control. Medium, titrated to pH 6.8 with NH$_4$OH, contains 0.2 M KH$_2$PO$_4$, 2.0 g/L citric acid, 2.0 g/L MgSO$_4$.7H$_2$0, 1.2 mL 98% H$_2$SO$_4$, 0.30 g/L ferric ammonium citrate, 0.20 g/L CaCl$_2$.2H$_2$O, 5 mL of trace metal mix, 5 g/L yeast extract, 10 g/L D-glucose, 30 g/L glycerol and 5 mg/L of either vitamin B$_{12}$ or hydroxocobalamin. Trace metal mix contains (g/L): Na$_2$SO$_4$ (4.0), MnSO$_4$ H$_2$0 (0.80), ZnSO$_4$ 7H$_2$0 (1.6), CoSO$_4$ (0.52), CuSO$_4$ 5H$_2$0 (0.12), and FeSO$_4$ 7H$_2$0 (4.0). In addition, the appropriate antibiotics are present in order to maintain plasmid stability.

Flasks are inoculated to an initial OD600 of approximately 0.01 AU, pH is maintained above pH 6.2 with the addition of 0.5 N KOH, and the glucose concentration is maintained above 2 g/L with the addition of a 50% (w/w) solution. pH is monitored using ColorpHast strips (EM Science, Gibbstown, N.J.). Glucose concentration is monitored using the Trinder enzymatic assay (Sigma, St. Louis, Mo.). At various times, aliquots are removed in order to determine 1,3-propanediol concentration (by gc or hplc analysis as described above) and cell density (OD$_{600}$). The strain FM5/pDT24 cotransformed with pAH61 and the cob(II)alamin reductase plasmid shows increased 1,3-propanediol production compared to the parent strain.

We claim:

1. A recombinant *E. coli* strain transformed with:
   (a) at least one copy of an exogenous gene encoding an enzyme having a glycerol dehydratase activity, whereby the glycerol dehydratase activity is expressed, and wherein said gene comprises the nucleotide sequence of SEQ ID NO:4, SEQ ID NO:5 or SEQ ID NO:6;
   (b) at least one copy of an exogenous gene encoding a protein having a 1,3-propanediol oxidoreductase activity, wherein said gene comprises the nucleotide sequence of SEQ ID NO:7; and
   (c) at least one copy of a gene encoding a protein having a cob(I)alamin adenosyltransferase activity whereby cob(I)alamin adenosyltransferase activity is increased and, wherein said gene comprises the nucleotide sequence SEQ ID NO:1, SEQ ID NO:2, or SEQ ID NO:3.

* * * * *

SEQUENCE LISTING

<160> NUMBER OF SEQ ID NOS: 26

<210> SEQ ID NO 1
<211> LENGTH: 591
<212> TYPE: DNA
<213> ORGANISM: Escherichia coli

<400> SEQUENCE: 1

| | | | | | | |
|---|---|---|---|---|---|---|
| atgagtgatg | aacgctacca | acagcgtcag | cagcgagtga | agaaaaagt | agatgctcgt | 60 |
| gtggcccagg | cccaggatga | acgcggtatt | atcatcgtct | ttaccggcaa | tggaaaaggc | 120 |
| aaaaccaccg | cggcatttgg | tacggcaaca | cgcgcagttg | gtcacggaaa | aaaagtaggc | 180 |
| gtcgtgcagt | ttattaaagg | cacctggcct | aatggcgaac | gcaatctgct | ggagccacat | 240 |
| ggcgttgagt | ttcaggtgat | ggcaacgggc | tttacctggg | atacacaaaa | ccgcgagtct | 300 |
| gataccgccg | cctgccgcga | agtctggcaa | catgcaaagc | ggatgcttgc | tgattcctca | 360 |
| ctggatatgg | ttttgcttga | tgaactgacg | tatatggtgg | cgtatgacta | tttgccactg | 420 |
| gaagaagtgg | tgcaggcgtt | aaatgaacgt | ccacatcaac | agacggtgat | tatcacgggt | 480 |
| cgtggttgtc | atcgggatat | tcttgaactg | gcagatacgg | taagtgaatt | acgccccgtc | 540 |
| aaacatgcgt | tgatgccggg | tgtaaaagcg | cagataggga | tcgattatta | a | 591 |

<210> SEQ ID NO 2
<211> LENGTH: 591
<212> TYPE: DNA
<213> ORGANISM: Salmonella typhimurium

<400> SEQUENCE: 2

| | | | | | | |
|---|---|---|---|---|---|---|
| atgagtgatg | aacgttatca | gcagcgccag | cagaaggtaa | agatcgggt | tgacgcccgt | 60 |
| gtcgcccagg | cacaggaaga | gcgcggtatt | attatcgtgt | ttactggcaa | tggtaagggc | 120 |
| aaaaccacgg | cggctttcgg | aactgccgcc | cgcgccgtag | gacacggtaa | aaacgtaggc | 180 |
| gtggtgcaat | ttattaaggg | cacctggcca | aacggcgagc | gtaatctgct | ggaaccgcat | 240 |
| ggcgtcgaat | ttcaggtgat | ggcaacggga | tttacctggg | agacgcaaaa | tcgcgaggca | 300 |
| gacaccgcag | catgtatggc | cgtttggcag | catgggaaac | ggatgctggc | cgatccgctg | 360 |
| cttgatatgg | tagtactgga | tgagctgacc | tatatggtgg | cgtatgacta | tttaccgctg | 420 |
| gaagaggtca | taagcgcgct | aaacgcgcgc | cctggtcacc | agacggtgat | tattacaggt | 480 |
| cgcggctgtc | accgggatat | tcttgatctt | gcggataccg | tcagcgaact | gcgtccggtt | 540 |
| aaacatgctt | tgacgcgggg | cgtaaaagcc | cagatgggaa | ttgattatta | a | 591 |

<210> SEQ ID NO 3
<211> LENGTH: 645
<212> TYPE: DNA
<213> ORGANISM: Pseudomonas denitrificans

<400> SEQUENCE: 3

| | | | | | | |
|---|---|---|---|---|---|---|
| atgagcgacg | agacgacagt | aggcggcgaa | gccccggccg | agaaggacga | tgcccgccac | 60 |
| gccatgaaga | tggcgaagaa | gaaggcagca | cgcgaaaaga | tcatggcgac | gaagaccgac | 120 |
| gagaagggtc | tgatcatcgt | caacaccggc | aaaggcaagg | gcaagtcgac | cgccggcttc | 180 |
| ggcatgatct | tccgccatat | cgcccacggc | atgcctgcg | ccgtcgtgca | gttcatcaag | 240 |
| ggtgcgatgt | caaccggcga | gcgcgagttg | atcgagaagc | atttcggcga | tgtctgccag | 300 |
| ttctacacgc | tcggcgaggg | cttcacctgg | gaaacgcagg | atcgcgcccg | cgatgttgcg | 360 |

```
atggctgaaa aggcctggga gaaggcgaag gaactgatcc gtgacgagcg caactcgatg    420
gtgctgctcg acgagatcaa cattgctctg cgctacgact acatcgacgt cgccgaagtg    480
gtgcgcttcc tgaaggaaga aaagccgcac atgacgcatg tggtgctcac cggccgcaac    540
gcgaaagaag acctgatcga agtcgccgat ctcgtcactg agatggagct gatcaagcat    600
ccgttccgtt ccggcatcaa ggcgcagcag ggcgtggagt tctga                    645

<210> SEQ ID NO 4
<211> LENGTH: 1668
<212> TYPE: DNA
<213> ORGANISM: Klebsiella pneumoniae

<400> SEQUENCE: 4
atgaaaagat caaaacgatt tgcagtactg gcccagcgcc ccgtcaatca ggacgggctg     60
attggcgagt ggcctgaaga ggggctgatc gccatggaca gcccctttga cccggtctct    120
tcagtaaaag tggacaacgg tctgatcgtc gaactggacg gcaaacgccg ggaccagttt    180
gacatgatcg accgatttat cgccgattac gcgatcaacg ttgagcgcac agagcaggca    240
atgcgcctgg aggcggtgga aatagcccgt atgctggtgg atattcacgt cagccgggag    300
gagatcattg ccatcactac cgccatcacg ccggccaaag cggtcgaggt gatggcgcag    360
atgaacgtgg tggagatgat gatggcgctg cagaagatgc gtgcccgccg acccccctcc    420
aaccagtgcc acgtcaccaa tctcaaagat aatccggtgc agattgccgc tgacgccgcc    480
gaggccggga tccgcggctt ctcagaacag agagaccacg tcggtatcgc gcgctacgcg    540
ccgtttaacg ccctggcgct gttggtcggt tcgcagtgcg gccgcccgg cgtgttgacg    600 cagtgctcgg tggaagaggc caccgagctg gagctgggca tgcgtggctt aaccagctac    660
gccgagacgg tgtcggtcta cggcaccgaa gcggtattta ccgacggcga tgatacgccg    720
tggtcaaagg cgttcctcgc ctcggcctac gcctcccgcg ggttgaaaat gcgctacacc    780
tccggcaccg atccgaagc gctgatgggc tattcggaga gcaagtcgat gctctacctc    840
gaatcgcgct gcatcttcat tactaaaggc gccggggttc agggactgca aaacggcgcg    900
gtgagctgta tcggcatgac cggcgctgtg ccgtcgggca ttcgggcggt gctggcggaa    960
aacctgatcg cctctatgct cgacctcgaa gtggcgtccg ccaacgacca gactttctcc   1020
cactcggata ttcgccgcac cgcgcgcacc ctgatgcaga tgctgccggg caccgacttt   1080
attttctccg gctacagcgc ggtgccgaac tacgacaaca tgttcgccgg ctcgaacttc   1140
gatgcggaag attttgatga ttacaacatc ctgcagcgtg acctgatggt tgacggcggc   1200
ctgcgtccgg tgaccgaggc ggaaaccatt gccattcgcc agaaagcggc gcgggcgatc   1260
caggcggttt tccgcgagct ggggctgccg ccaatcgccg acgaggaggt ggaggccgcc   1320
acctacgcgc acggcagcaa cgagatgccg ccgcgtaacg tggtgaagga tctgagtgcg   1380
gtggaagaga tgatgaagcg caacatcacc ggcctcgata ttgtcggcgc gctgagccgc   1440
agcggctttg aggatatcgc cagcaatatt ctcaatatgc tgccgcagcg ggtcaccggc   1500
gattacctgc agacctcggc cattctcgat cggcagttcg aggtggtgag tgcggtcaac   1560
gacatcaatg actatcaggg gccgggcacc ggctatcgca tctctgccga acgctgggcg   1620
gagatcaaaa atattccggg cgtggttcag cccgacacca ttgaataa                1668

<210> SEQ ID NO 5
<211> LENGTH: 585
<212> TYPE: DNA
```

<213> ORGANISM: Klebsiella pneumoniae

<400> SEQUENCE: 5

| | |
|---|---|
| gtgcaacaga caacccaaat tcagccctct tttaccctga aaacccgcga gggcggggta | 60 |
| gcttctgccg atgaacgcgc cgatgaagtg gtgatcggcg tcggccctgc cttcgataaa | 120 |
| caccagcatc acactctgat cgatatgccc catggcgcga tcctcaaaga gctgattgcc | 180 |
| ggggtggaag aagaggggct tcacgcccgg gtggtgcgca ttctgcgcac gtccgacgtc | 240 |
| tcctttatgg cctgggatgc ggccaacctg agcggctcgg ggatcggcat cggtatccag | 300 |
| tcgaagggga ccacggtcat ccatcagcgc gatctgctgc cgctcagcaa cctggagctg | 360 |
| ttctcccagg cgccgctgct gacgctggag acctaccggc agattggcaa aaacgctgcg | 420 |
| cgctatgcgc gcaaagagtc accttcgccg gtgccggtgg tgaacgatca gatggtgcgg | 480 |
| ccgaaattta tggccaaagc cgcgctattt catatcaaag agaccaaaca tgtggtgcag | 540 |
| gacgccgagc ccgtcaccct gcacatcgac ttagtaaggg agtga | 585 |

<210> SEQ ID NO 6
<211> LENGTH: 426
<212> TYPE: DNA
<213> ORGANISM: Klebsiella pneumoniae

<400> SEQUENCE: 6

| | |
|---|---|
| atgagcgaga aaaccatgcg cgtgcaggat tatccgttag ccacccgctg cccggagcat | 60 |
| atcctgacgc ctaccggcaa accattgacc gatattaccc tcgagaaggt gctctctggc | 120 |
| gaggtgggcc cgcaggatgt gcggatctcc cgccagaccc ttgagtacca ggcgcagatt | 180 |
| gccgagcaga tgcagcgcca tgcggtggcg cgcaatttcc gccgcgcggc ggagcttatc | 240 |
| gccattcctg acgagcgcat tctggctatc tataacgcgc tgcgcccgtt ccgctcctcg | 300 |
| caggcggagc tgctggcgat cgccgacgag ctggagcaca cctggcatgc gacagtgaat | 360 |
| gccgcctttg tccgggagtc ggcggaagtg tatcagcagc ggcataagct gcgtaaagga | 420 |
| agctaa | 426 |

<210> SEQ ID NO 7
<211> LENGTH: 1164
<212> TYPE: DNA
<213> ORGANISM: Klebsiella pneumoniae

<400> SEQUENCE: 7

| | |
|---|---|
| atgagctatc gtatgtttga ttatctggtg ccaaacgtta acttttttgg ccccaacgcc | 60 |
| atttccgtag tcggcgaacg ctgccagctg ctggggggga aaaagccct gctggtcacc | 120 |
| gacaaaggcc tgcgggcaat taagatggc gcggtggaca aaaccctgca ttatctgcgg | 180 |
| gaggccggga tcgaggtggc gatctttgac ggcgtcgagc cgaacccgaa agacaccaac | 240 |
| gtgcgcgacg gcctcgccgt gtttcgccgc gaacagtgcg acatcatcgt caccgtgggc | 300 |
| ggcggcagcc cgcacgattg cggcaaaggc atcggcatcg ccgccaccca tgagggcgat | 360 |
| ctgtaccagt atgccggaat cgagaccctg accaacccgc tgccgcctat cgtcgcggtc | 420 |
| aataccaccg ccggcaccgc cagcgaggtc acccgccact gcgtcctgac aacaccgaa | 480 |
| accaaagtga agtttgtgat cgtcagctgg cgcaaactgc cgtcggtctc tatcaacgat | 540 |
| ccactgctga tgatcggtaa accggccgcc ctgaccgcgg cgaccgggat ggatgccctg | 600 |
| acccacgccg tagaggccta tatctccaaa gacgctaacc cggtgacgga cgccgccgcc | 660 |
| atgcaggcga tccgcctcat cgcccgcaac ctgcgccagg ccgtggccct cggcagcaat | 720 |

-continued

```
ctgcaggcgc gggaaaacat ggcctatgct tctctgctgg ccgggatggc tttcaataac    780
gccaacctcg gctacgtgca cgccatggcg caccagctgg gcggcctgta cgacatgccg    840
cacggcgtgg ccaacgctgt cctgctgccg catgtggcgc gctacaacct gatcgccaac    900
ccggagaaat cgccgatat cgctgaactg atgggcgaaa atatcaccgg actgtccact    960
ctcgacgcgg cggaaaaagc catcgccgct atcacgcgtc tgtcgatgga tatcggtatt   1020
ccgcagcatc tgcgcgatct gggggtaaaa gaggccgact tccctacat ggcggagatg    1080 gctctaaaag acggcaatgc gttctcgaac ccgcgtaaag caacgagca ggagattgcc    1140 gcgattttcc gccaggcatt ctga                                          1164
```

<210> SEQ ID NO 8
<211> LENGTH: 18
<212> TYPE: DNA
<213> ORGANISM: Artificial Sequence
<220> FEATURE:
<223> OTHER INFORMATION: Universal Primer
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is a, c, g, or t

<400> SEQUENCE: 8

```
atggaraara cscgnctn                                                  18
```

<210> SEQ ID NO 9
<211> LENGTH: 759
<212> TYPE: DNA
<213> ORGANISM: Escherichia coli

<400> SEQUENCE: 9

```
atgcattacc agccaaaaca agatttactc aatgatcgca ttatcctggt gacgggagcc    60
agcgatggta ttggtcgtga agccgcgatg acgtatgcac gctatggtgc gacagtgatt   120
ctgttgggcc gtaatgaaga aaaattacgt caggtagcca gccacataaa cgaagaaact   180
gggcgtcagc cacagtggtt tattctcgat ttgctgacct gcacgtccga aaattgccaa   240
caactggcac agcgcattgc cgttaattat ccgcgtctgg atggtgtttt gcataatgcc   300
ggattgctcg cgatgtttg cccaatgagc gaacaaaatc cgcaggtctg caggacgtc    360 atgcaggtca acgttaatgc cacctttatg ctcacccagg cactgcttcc tttattactc   420
aaatcggacg ccggttcact ggtctttact tcatcaagcg ttggacgtca gggacgagcc   480
aactggggtg catatgcagc gtcgaaattt gccaccgaag ggatgatgca ggtactggcc   540
gatgaatatc agcagcgcct gcgtgtcaac tgcattaacc caggcggtac gcgcaccgca   600
atgcgtgcca gcgccttccc gaccgaagat ccacagaaac ttaaacaccc gctgatatc   660 atgccgctct acctctggct gatgggcgat gacagccgcc gtaaaaccgg catgaccttt   720
gacgcccaac cgggccgtaa accaggaatt tcccaatga                          759
```

-continued

<210> SEQ ID NO 10
<211> LENGTH: 12145
<212> TYPE: DNA
<213> ORGANISM: Artificial Sequence
<220> FEATURE:
<223> OTHER INFORMATION: Plasmid

<400> SEQUENCE: 10

| | | | | | |
|---|---|---|---|---|---|
| gtcgaccacc | acggtggtga | ctttaatgcc | gctctcatgc | agcagctcgg | tggcggtctc | 60 |
| aaaattcagg | atgtcgccgg | tatagttttt | gataatcagc | aagacgcctt | cgccgccgtc | 120 |
| aatttgcatc | gcgcattcaa | acattttgtc | cggcgtcggc | gaggtgaata | tttccccgg | 180 |
| acaggcgccg | gagagcatgc | cctggccgat | atagccgcag | tgcatcggtt | catgtccgct | 240 |
| gccgccgccg | gagagcaggg | ccaccttgcc | agccaccggc | gcgtcggtgc | gggtcacata | 300 |
| cagcgggtcc | tgatgcaggg | tcagctgcgg | atgggcttta | gccagcccct | gtaattgttc | 360 |
| attcagtaca | tcttcaacac | ggttaatcag | cttttcatt | attcagtgct | ccgttggaga | 420 |
| aggttcgatg | ccgcctctct | gctggcggag | gcggtcatcg | cgtagggta | tcgtctgacg | 480 |
| gtggagcgtg | cctggcgata | tgatgattct | ggctgagcgg | acgaaaaaaa | gaatgccccg | 540 |
| acgatcgggt | tcattacga | aacattgctt | cctgattttg | tttctttatg | gaacgttttt | 600 |
| gctgaggata | tggtgaaaat | gcgagctggc | gcgcttttt | tcttctgcca | taagcggcgg | 660 |
| tcaggatagc | cggcgaagcg | ggtgggaaaa | aattttttgc | tgattttctg | ccgactgcgg | 720 |
| gagaaaaggc | ggtcaaacac | ggaggattgt | aagggcatta | tgcggcaaag | gagcggatcg | 780 |
| ggatcgcaat | cctgacagag | actagggttt | tttgttccaa | tatggaacgt | aaaaaattaa | 840 |
| cctgtgtttc | atatcagaac | aaaaaggcga | agatttttt | tgttccctgc | ggccctaca | 900 |
| gtgatcgcac | tgctccggta | cgctccgttc | aggccgcgct | tcactggccg | gcgcggataa | 960 |
| cgccagggct | catcatgtct | acatgcgcac | ttatttgagg | gtgaaaggaa | tgctaaaagt | 1020 |
| tattcaatct | ccagccaaat | atcttcaggg | tcctgatgct | gctgttctgt | tcggtcaata | 1080 |
| tgccaaaaac | ctggcggaga | gcttcttcgt | catcgctgac | gatttcgtaa | tgaagctggc | 1140 |
| gggagagaaa | gtggtgaatg | gcctgcagag | ccacgatatt | cgctgccatg | cggaacggtt | 1200 |
| taacggcgaa | tgcagccatg | cggaaatcaa | ccgtctgatg | gcgattttgc | aaaaacaggg | 1260 |
| ctgccgcggc | gtggtcggga | tcggcggtgg | taaaaccctc | gataccgcga | aggcgatcgg | 1320 |
| ttactaccag | aagctgccgg | tggtggtgat | cccgaccatc | gcctcgaccg | atgcgccaac | 1380 |
| cagcgcgctg | tcggtgatct | acaccgaagc | gggcgagttt | gaagagtatc | tgatctatcc | 1440 |
| gaaaaacccg | gatatggtgg | tgatggacac | ggcgattatc | gccaaagcgc | cggtacgcct | 1500 |
| gctggtctcc | ggcatgggcg | atgcgctctc | cacctggttc | gaggccaaag | cttgctacga | 1560 |
| tgcgcgcgcc | accagcatgg | ccggaggaca | gtccaccgag | gcggcgctga | gcctcgcccg | 1620 |
| cctgtgctat | gatacgctgc | tggcggaggg | cgaaaaggcc | cgtctggcgg | cgcaggccgg | 1680 |
| ggtagtgacc | gaagcgctgg | agcgcatcat | cgaggcgaac | acttacctca | gcggcattgg | 1740 |
| ctttgaaagc | agtggcctgg | ccgctgccca | tgcaatccac | aacggtttca | ccattcttga | 1800 |
| agagtgccat | cacctgtatc | acggtgagaa | agtggccttc | ggtacctgg | cgcagctggt | 1860 |
| gctgcagaac | agcccgatgg | acgagattga | aacggtgcag | gcttctgcc | agcgcgtcgg | 1920 |
| cctgccggtg | acgctcgcgc | agatgggcgt | caaagagggg | atcgacgaga | aaatcgccgc | 1980 |
| ggtggcgaaa | gctacctgcg | cggaagggga | aaccatccat | aatatgccgt | tgcggtgac | 2040 |
| cccggagagc | gtccatgccg | ctatcctcac | cgccgatctg | ttaggccagc | agtggctggc | 2100 |

```
gcgttaattc gcggtggcta aaccgctggc ccaggtcagc ggttttcctt tctccctcc   2160
ggcagtcgct gccggagggg ttctctatgg tacaacgcgg aaaggatat gactgttcag   2220
actcaggata ccgggaaggc ggtctcttcc gtcattgccc agtcatggca ccgctgcagc   2280
aagtttatgc agcgcgaaac ctggcaaacg ccgcaccagg cccagggcct gaccttcgac   2340
tccatctgtc ggcgtaaaac cgcgctgctc accatcggcc aggcggcgct ggaagacgcc   2400
tgggagttta tggacggccg cccctgcgcg ctgtttattc ttgatgagtc cgcctgcatc   2460
ctgagccgtt gcggcgagcc gcaaaccctg gcccagctgg ctgccctggg atttcgcgac   2520
ggcagctatt gtgcggagag cattatcggc acctgcgcgc tgtcgctggc cgcgatgcag   2580
ggccagccga tcaacaccgc cggcgatcgg cattttaagc aggcgctaca gccatggagt   2640
ttttgctcga cgccggtgtt tgataaccac gggcggctgt tcggctctat ctcgctttgc   2700
tgtctggtcg agcaccagtc cagcgccgac ctctccctga cgctggccat cgcccgcgag   2760
gtgggtaact ccctgcttac cgacagcctg ctggcggaat ccaaccgtca cctcaatcag   2820
atgtacggcc tgctggagag catggacgat ggggtgatgg cgtggaacga acagggcgtg   2880
ctgcagtttc tcaatgttca ggcggcgaga ctgctgcatc ttgatgctca ggccagccag   2940
gggaaaaata tcgccgatct ggtgaccctc ccggcgctgc tgcgccgcgc catcaaacac   3000
gcccgcggcc tgaatcacgt cgaagtcacc tttgaaagtc agcatcagtt tgtcgatgcg   3060
gtgatcacct aaaaccgat tgtcgaggcg caaggcaaca gttttattct gctgctgcat   3120
ccggtggagc agatgcggca gctgatgacc agccagctcg gtaaagtcag ccacaccttt   3180
gagcagatgt ctgccgacga tccggaaacc cgacgcctga tccactttgg ccgccaggcg   3240
gcgcgcggcg gcttcccggt gctactgtgc ggcgaagagg gggtcgggaa agagctgctg   3300
agccaggcta ttcacaatga aagcgaacgg gcgggcggcc cctacatctc cgtcaactgc   3360
cagctatatg ccgacagcgt gctgggccag gactttatgg gcagcgcccc taccgacgat   3420
gaaaatggtc gcctgagccg ccttgagctg gccaacggcg gcaccctgtt tctggaaaag   3480
atcgagtatc tggcgccgga gctgcagtcg gctctgctgc aggtgattaa gcagggcgtg   3540
ctcacccgcc tcgacgcccg cgcctgatc ccggtggatg tgaaggtgat gccaccacc    3600
accgtcgatc tggccaatct ggtggaacag aaccgcttta ccgccagct gtactatgcg   3660
ctgcactcct ttgagatcgt catcccgccg ctgcgcgccc gacgcaacag tattccgtcg   3720
ctggtgcata accggttgaa gagcctggag aagcgttcct cttcgcgact gaaagtggac   3780
gatgacgcgc tggcacagct ggtggcctac tcgtggccgg ggaatgattt tgagctcaac   3840
agcgtcattg agaatatcgc catcagcagc gacaacggcc acattcgcct gagtaatctg   3900
ccggaatatc tcttttccga gcggccgggc ggggatagcg cgtcatcgct gctgccggcc   3960
agcctgactt ttagcgccat cgaaaaggaa gctattattc acgccgcccg ggtgaccagc   4020
gggcgggtgc aggagatgtc gcagctgctc aatatcggcc gcaccaccct gtggcgcaaa   4080
atgaagcagt acgatattga cgccagccag ttcaagcgca agcatcaggc ctagtctctt   4140
cgattcgcgc catggagaac agggcatccg acaggcgatt gctgtagcgt ttgagcgcgt   4200
cgcgcagcgg atgcgcgcgg tccatggccg tcagcaggcg ttcgagccga cgggactggg   4260
tgcgcgccac gtgcagctgg gcagaggcga gattcctccc cgggatcacg aactgtttta   4320
acgggccgct ctcggccata ttgcggtcga taagccgctc cagggcggtg atctcctctt   4380
cgccgatcgt ctggctcagg cgggtcaggc cccgcgcatc gctggccagt tcagccccca   4440
```

-continued

```
gcacgaacag cgtctgctga atatggtgca ggctttcccg cagcccggcg tcgcgggtcg    4500
tggcgtagca gacgcccagc tgggatatca gttcatcgac ggtgccgtag gcctcgacgc    4560
gaatatggtc tttctcgatg cggctgccgc cgtacagggc ggtggtgcct ttatccccgg    4620
tgcgggtata gatacgatac attcagtttc tctcacttaa cggcaggact ttaaccagct    4680
gcccggcgtt ggcgccgagc gtacgcagtt gatcgtcgct atcggtgacg tgtccggtag    4740
ccagcggcgc gtccgccggc agctgggcat gagtgagggc tatctcgccg gacgcgctga    4800
gcccgatacc cacccgcagg ggcgagcttc tggccgccag ggcgcccagc gcagcggcgt    4860
caccgcctcc gtcataggtt atggtctggc aggggacccc ctgctcctcc agcccccagc    4920
acagctcatt gatggcgccg gcatggtgcc cgcgcggatc gtaaaacagg cgtacgcctg    4980
gcggtgaaag cgacatgacg gtcccctcgt taacactcag aatgcctggc ggaaaatcgc    5040
ggcaatctcc tgctcgttgc ctttacgcgg gttcgagaac gcattgccgt cttttagagc    5100
catctccgcc atgtagggga agtcggcctc ttttaccccc agatcgcgca gatgctgcgg    5160
aataccgata tccatcgaca gacgcgtgat agcggcgatg cttttttccg ccgcgtcgag    5220
agtggacagt ccggtgatat tttcgcccat cagttcagcg atatcggcga atttctccgg    5280
gttggcgatc aggttgtagc gcgccacatg cggcagcagg acagcgttgg ccacgccgtg    5340
cggcatgtcg tacaggccgc ccagctggtg cgccatggcg tgcacgtagc cgaggttggc    5400
gttattgaaa gccatcccgg ccagcagaga agcataggcc atgttttccc gcgcctgcag    5460
attgctgccg agggccacgg cctggcgcag gttgcgggcg atgaggcgga tcgcctgcat    5520
ggcggcggcg tccgtcaccg ggttagcgtc tttggagata taggcctcta cggcgtgggt    5580
cagggcatcc atcccggtcg ccgcggtcag ggcggccggt ttaccgatca tcagcagtgg    5640
atcgttgata gagaccgacg gcagtttgcg ccagctgacg atcacaaact tcactttggt    5700
ttcggtgttg gtcaggacgc agtggcgggt gacctcgctg gcggtgccgg cggtggtatt    5760
gaccgcgacg ataggcggca gcgggttggt cagggtctcg attccggcat actggtacag    5820
atcgccctca tgggtggcgg cgatgccgat gcctttgccg caatcgtgcg ggctgccgcc    5880
gcccacggtg acgatgatgt cgcactgttc gcggcgaaac acggcgaggc cgtcgcgcac    5940
gttggtgtct ttcgggttcg gctcgacgcc gtcaaagatc gccacctcga tcccggcctc    6000
ccgcagataa tgcagggttt tgtccaccgc gccatcttta attgcccgca ggcctttgtc    6060
ggtgaccagc agggcttttt tccccccag cagctggcag cgttcgccga ctacggaaat    6120
ggcgttgggg ccaaaaaagt taacgtttgg caccagataa tcaaacatac gatagctcat    6180 aatataccttc tcgcttcag gttataatgc ggaaaaacaa tccagggcgc actgggctaa    6240
taattgatcc tgctcgaccg taccgccgct aacgccgacg gcgccaatta cctgctcatt    6300
aaaaataact ggcaggccgc cgccaaaaat aataattcgc tgttggttgg ttagctgcag    6360
accgtacaga gattgtcctg gctggaccgc tgacgtaatt tcatgggtac cttgcttcag    6420
gctgcaggcg ctccaggctt tattcaggga aatatcgcag ctggagacga aggcctcgtc    6480
catccgctgg ataagcagcg tgttgcctcc gcggtcaact acggaaaaca ccaccgccac    6540
gttgatctca gtggctttt tttccaccgc cgccgccatt tgctgggcgg cggccagggt    6600
gattgtctga acttgttggc tcttgttcat cattctctcc cgcaccagga taacgctggc    6660
gcgaatagtc agtaggggc gatagtaaaa aactattacc attcggttgg cttgctttat    6720
ttttgtcagc gttattttgt cgcccgccat gatttagtca ataggttaa aatagcgtcg    6780 gaaaaacgta attaagggcg ttttttatta attgatttat atcattgcgg gcgatcacat    6840
```

-continued

```
tttttatttt tgccgccgga gtaaagtttc atagtgaaac tgtcggtaga tttcgtgtgc      6900
caaattgaaa cgaaattaaa tttatttttt tcaccactgg ctcatttaaa gttccgctat      6960
tgccggtaat ggccgggcgg caacgacgct ggccggcgt attcgctacc gtctgcggat       7020
ttcaccttt gagccgatga acaatgaaaa gatcaaaacg atttgcagta ctggcccagc       7080
gccccgtcaa tcaggacggg ctgattggcg agtggcctga agaggggctg atcgccatgg      7140
acagccctt tgacccggtc tcttcagtaa aagtggacaa cggtctgatc gtcgaactgg       7200
acggcaaacg ccgggaccag tttgacatga tcgaccgatt tatcgccgat tacgcgatca     7260
acgttgagcg cacagagcag gcaatgcgcc tggaggcggt ggaaatagcc cgtatgctgg      7320
tggatattca cgtcagccgg gaggagatca ttgccatcac taccgccatc acgccggcca     7380
aagcggtcga ggtgatggcg cagatgaacg tggtggagat gatgatggcg ctgcagaaga     7440
tgcgtgcccg ccggaccccc tccaaccagt gccacgtcac caatctcaaa gataatccgg     7500
tgcagattgc cgctgacgcc gccgaggccg ggatccgcgg cttctcagaa caggagacca     7560
cggtcggtat cgcgcgctac cgccgtttta acgccctggc gctgttggtc ggttcgcagt     7620
gcggccgccc cggcgtgttg acgcagtgct cggtggaaga ggccaccgag ctggagctgg     7680
gcatgcgtgg cttaaccagc tacgccgaga cggtgtcggt ctacggcacc gaagcggtat    7740
ttaccgacgg cgatgatacg ccgtggtcaa aggcgttcct cgcctcggcc tacgcctccc    7800
gcgggttgaa aatgcgctac acctccggca ccggatccga agcgctgatg ggctattcgg     7860
agagcaagtc gatgctctac ctcgaatcgc gctgcatctt cattactaaa ggcgccgggg    7920
ttcagggact gcaaaacggc gcggtgagct gtatcggcat gaccggcgct gtgccgtcgg     7980
gcattcgggc ggtgctggcg gaaaaacctga tcgcctctat gctcgacctc gaagtggcgt    8040
ccgccaacga ccagacttc tcccactcgg atattcgccg caccgcgcgc accctgatgc      8100
agatgctgcc gggcaccgac tttatttct ccggctacag cgcggtgccg aactacgaca      8160
acatgttcgc cggctcgaac ttcgatgcgg aagattttga tgattacaac atcctgcagc     8220
gtgacctgat ggttgacggc ggcctgcgtc cggtgaccga ggcggaaacc attgccattc     8280
gccagaaagc ggcgcgggcg atccaggcgg ttttccgcga gctggggctg ccgccaatcg     8340
ccgacgagga ggtggaggcc gccacctacg cgcacggcag caacgagatg ccgccgcgta    8400
acgtggtgga ggatctgagt gcggtggaag agatgatgaa gcgcaacatc accggcctcg    8460
atattgtcgg cgcgctgagc cgcagcggct ttgaggatat cgccagcaat attctcaata    8520
tgctgcgcca gcggtcacc ggcgattacc tgcagacctc ggccattctc gatcggcagt      8580
tcgaggtggt gagtgcggtc aacgacatca atgactatca ggggccgggc accggctatc    8640
gcatctctgc cgaacgctgg gcggagatca aaaatattcc gggcgtggtt cagcccgaca    8700
ccattgaata aggcggtatt cctgtgcaac agacaaccca aattcagccc tcttttaccc     8760
tgaaaacccg cgagggcggg gtagcttctg ccgatgaacg cgccgatgaa gtggtgatcg    8820
gcgtcggccc tgccttcgat aaacaccagc atcacactct gatcgatatg ccccatggcg    8880
cgatcctcaa agagctgatt gccggggtgg aagaagaggg gcttcacgcc cggtggtgc      8940
gcattctgcg cacgtccgac gtctccttta tggcctggga tcggccaac ctgagcggct      9000
cggggatcgg catcggtatc cagtcgaagg ggaccacggt catccatcag cgcgatctgc     9060
tgccgctcag caacctggag ctgttctccc aggcgccgct gctgacgctg gagacctacc    9120
ggcagattgg caaaaacgct gcgcgctatg cgcgcaaaga gtcaccttcg ccggtgccgg     9180
```

-continued

| | |
|---|---|
| tggtgaacga tcagatggtg cggccgaaat ttatggccaa agccgcgcta tttcatatca | 9240 |
| aagagaccaa acatgtggtg caggacgccg agcccgtcac cctgcacatc gacttagtaa | 9300 |
| gggagtgacc atgagcgaga aaaccatgcg cgtgcaggat tatccgttag ccacccgctg | 9360 |
| cccggagcat atcctgacgc ctaccggcaa accattgacc gatattaccc tcgagaaggt | 9420 |
| gctctctggc gaggtgggcc cgcaggatgt gcggatctcc cgccagaccc ttgagtacca | 9480 |
| ggcgcagatt gccgagcaga tgcagcgcca tgcggtggcg cgcaatttcc gccgcgcggc | 9540 |
| ggagcttatc gccattcctg acgagcgcat tctggctatc tataacgcgc tgcgcccgtt | 9600 |
| ccgctcctcg caggcggagc tgctggcgat cgccgacgag ctggagcaca cctggcatgc | 9660 |
| gacagtgaat gccgccttttg tccgggagtc ggcggaagtg tatcagcagc ggcataagct | 9720 |
| gcgtaaagga agctaagcgg aggtcagcat gccgttaata gccgggattg atatcggcaa | 9780 |
| cgccaccacc gaggtggcgc tggcgtccga ctacccgcag gcgagggcgt tgttgccag | 9840 |
| cgggatcgtc gcgacgacgg gcatgaaagg gacgcgggac aatatcgccg ggaccctcgc | 9900 |
| cgcgctggag caggccctgg cgaaaacacc gtggtcgatg agcgatgtct ctcgcatcta | 9960 |
| tcttaacgaa gccgcgccgg tgattggcga tgtggcgatg gagaccatca ccgagaccat | 10020 |
| tatcaccgaa tcgaccatga tcggtcataa cccgcagacg ccgggcgggg tgggcgttgg | 10080 |
| cgtggggacg actatcgccc tcgggcggct ggcgacgctg ccggcggcgc agtatgccga | 10140 |
| ggggtggatc gtactgattg acgacgccgt cgatttcctt gacgccgtgt ggtggctcaa | 10200 |
| tgaggcgctc gaccgggga tcaacgtggt ggcggcgatc ctcaaaaagg acgacggcgt | 10260 |
| gctggtgaac aaccgcctgc gtaaaaccct gccggtggtg gatgaagtga cgctgctgga | 10320 |
| gcaggtcccc gaggggggtaa tggcggcggt ggaagtggcc gcgccgggcc aggtggtgcg | 10380 |
| gatcctgtcg aatccctacg ggatcgccac cttcttcggg ctaagcccgg aagagaccca | 10440 |
| ggccatcgtc cccatcgccc gcgccctgat tggcaaccgt tccgcggtgg tgctcaagac | 10500 |
| cccgcagggg gatgtgcagt cgcgggtgat cccggcgggc aacctctaca ttagcggcga | 10560 |
| aaagcgccgc ggagaggccg atgtcgccga gggcgcggaa gccatcatgc aggcgatgag | 10620 |
| cgcctgcgct ccggtacgcg acatccgcgg cgaaccgggc acccacgccg gcggcatgct | 10680 |
| tgagcgggtg cgcaaggtaa tggcgtccct gaccggccat gagatgagcg cgatatacat | 10740 |
| ccaggatctg ctggcggtgg atacgtttat tccgcgcaag gtgcagggcg ggatggccgg | 10800 |
| cgagtgcgcc atggagaatg ccgtcgggat ggcggcgatg gtgaaagcgg atcgtctgca | 10860 |
| aatgcaggtt atcgcccgcg aactgagcgc ccgactgcag accgaggtgg tggtgggcga | 10920 |
| cgtggaggcc aacatggcca tcgccggggc gttaaccact cccggctgtg cggcgccgct | 10980 |
| ggcgatcctc gacctcggcg ccggctcgac ggatgcggca atcgtcaacg cggaggggca | 11040 |
| gataacggcg gtccatctcg ccggggcggg gaatatggtc agcctgttga ttaaaaccga | 11100 |
| gctgggcctc gaggatcttt cgctggcgga agcgataaaa aaatacccgc tggccaaagt | 11160 |
| ggaaagcctg ttcagtattc gtcacgagaa tggcgcggtg gagttctttc gggaagccct | 11220 |
| cagcccggcg gtgttcgcca aagtggtgta catcaaggag ggcgaactgg tgccgatcga | 11280 |
| taacgccagc ccgctggaaa aaattcgtct cgtgcgccgg caggcgaaag agaaagtgtt | 11340 |
| tgtcaccaac tgcctgcgcg cgctgcgcca ggtctcaccc ggcggttcca ttcgcgatat | 11400 |
| cgcctttgtg gtgctggtgg gcggctcatc gctggacttt gagatcccgc agcttatcac | 11460 |
| ggaagccttg tcgcactatg gcgtggtcgc cgggcagggc aatattcggg gaacagaagg | 11520 |
| gccgcgcaat gcggtcgcca ccgggctgct actggccggt caggcgaatt aaacgggcgc | 11580 |

-continued

```
tcgcgccagc ctctctcttt aacgtgctat ttcaggatgc cgataatgaa ccagacttct    11640
accttaaccg ggcagtgcgt ggccgagttt cttggcaccg gattgctcat tttcttcggc    11700
gcgggctgcg tcgctgcgct gcgggtcgcc ggggccagct ttggtcagtg ggagatcagt    11760
attatctggg gccttggcgt cgccatggcc atctacctga cggccggtgt ctccggcgcg    11820
cacctaaatc cggcggtgac cattgccctg tggctgttcg cctgttttga acgccgcaag    11880
gtgctgccgt ttattgttgc ccagacggcc ggggccttct cgccgccgc gctggtgtat     11940 gggctctatc gccagctgtt tctcgatctt gaacagagtc agcatatcgt gcgcggcact    12000
gccgccagtc ttaacctggc cggggtcttt tccacgtacc cgcatccaca tatcactttt    12060
atacaagcgt ttgccgtgga gaccaccatc acggcaatcc tgatggcgat gatcatggcc    12120
ctgaccgacg acggcaacgg aattc                                         12145
```

<210> SEQ ID NO 11
<211> LENGTH: 94
<212> TYPE: DNA
<213> ORGANISM: Artificial Sequence
<220> FEATURE:
<223> OTHER INFORMATION: Sequence used for construction of pTacIQ

<400> SEQUENCE: 11

```
agcttaggag tctagaatat tgagctcgaa ttcccgggca tgcggtaccg gatccagaaa      60
aaagcccgca cctgacagtg cgggcttttt tttt                                  94
```

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12

```
ggaattcaga tctcagcaat gagcgagaaa accatgc                               37
```

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13

```
gctctagatt agcttccttt acgcagc                                          27
```

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14

```
ggccaagctt aaggaggtta attaaatgaa aag                                   33
```

<210> SEQ ID NO 15
<211> LENGTH: 26
<212> TYPE: DNA
<213> ORGANISM: Artificial Sequence
<220> FEATURE:
<223> OTHER INFORMATION: Primer

```
<400> SEQUENCE: 15
gctctagatt attcaatggt gtcggg                                          26

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
gcgccgtcta gaattatgag ctatcgtatg tttgattatc tg                        42

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
tctgatacgg gatcctcaga atgcctggcg gaaaat                               36

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tcgacgaatt caggagga                                                   18

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
ctagtcctcc tgaattcg                                                   18

<210> SEQ ID NO 20
<211> LENGTH: 4549
<212> TYPE: DNA
<213> ORGANISM: Artificial Sequence
<220> FEATURE:
<223> OTHER INFORMATION: Sequence used in insert for pCL1920

<400> SEQUENCE: 20
agctcgtcag cgggtgttgg cgggtgtcgg ggctggctta actatgcggc atcagagcag      60
attgtactga gagtgcacca tatgcggtgt gaaataccgc acagatgcgt aaggagaaaa     120
taccgcatca ggcgccattc gccattcagg ctgcgcaact gttgggaagg gcgatcggtg     180
cgggcctctt cgctattacg ccagctggcg aaagggggat gtgctgcaag gcgattaagt     240
tgggtaacgc cagggttttc ccagtcacga cgttgtaaaa cgacggccag tgaattcgag     300
ctcggtaccc gggatcctc tagagtcgac ctgcaggcat gcaagcttgg cgtaatcatg     360
gtcatagctg tttcctgtgt gaaattgtta tccgctcaca attccacaca acatacgagc     420
cggaagcata aagtgtaaag cctggggtgc ctaatgagtg agctaactca cattaattgc     480
gttgcgctca ctgcccgctt tccagtcggg aaacctgtcg tgccagctgc attaatgaat     540
```

-continued

```
cggccaacgc gaattcccga cagtaagacg ggtaagcctg ttgatgatac cgctgcctta    600
ctgggtgcat tagccagtct gaatgacctg tcacgggata atccgaagtg gtcagactgg    660
aaaatcagag ggcaggaact gctgaacagc aaaaagtcag atagcaccac atagcagacc    720
cgccataaaa cgccctgaga agcccgtgac gggcttttct tgtattatgg gtagtttcct    780
tgcatgaatc cataaaaggc gcctgtagtg ccatttaccc ccattcactg ccagagccgt    840
gagcgcagcg aactgaatgt cacgaaaaag acagcgactc aggtgcctga tggtcggaga    900
caaaaggaat attcagcgat ttgcccgagc ttgcgagggt gctacttaag cctttagggt    960
tttaaggtct gttttgtaga ggagcaaaca gcgtttgcga catccttttg taatactgcg   1020
gaactgacta aagtagtgag ttatacacag ggctgggatc tattctttt  atcttttttt   1080 attctttctt tattctataa attataacca cttgaatata aacaaaaaaa acacacaaag   1140
gtctagcgga atttacagag ggtctagcag aatttacaag ttttccagca aaggtctagc   1200
agaatttaca gatacccaca actcaaagga aaaggactag taattatcat tgactagccc   1260
atctcaattg gtatagtgat taaaatcacc tagaccaatt gagatgtatg tctgaattag   1320
ttgttttcaa agcaaatgaa ctagcgatta gtcgctatga cttaacggag catgaaacca   1380
agctaatttt atgctgtgtg gcactactca accccacgat tgaaacccct acaaggaaag   1440
aacggacggt atcgttcact tataaccaat acgctcagat gatgaacatc agtagggaaa   1500
atgcttatgg tgtattagct aaagcaacca gagagctgat gacgagaact gtggaaatca   1560
ggaatccttt ggttaaaggc tttgagattt tccagtggac aaactatgcc aagttctcaa   1620
gcgaaaaatt agaattagtt tttagtgaag agatattgcc ttatcttttc cagttaaaaa   1680
aattcataaa atataatctg gaacatgtta agtcttttga aaacaaatac tctatgagga   1740
tttatgagtg gttattaaaa gaactaacac aaaagaaaac tcacaaggca aatatagaga   1800
ttagccttga tgaatttaag ttcatgttaa tgcttgaaaa taactaccat gagtttaaaa   1860
ggcttaacca atgggttttg aaaccaataa gtaaagattt aaacacttac agcaatatga   1920
aattggtggt tgataagcga ggccgcccga ctgatacgtt gattttccaa gttgaactag   1980
atagacaaat ggatctcgta accgaacttg agaacaacca gataaaaatg aatggtgaca   2040
aaataccaac aaccattaca tcagattcct acctacataa cggactaaga aaaacactac   2100
acgatgcttt aactgcaaaa attcagctca ccagttttga ggcaaaattt ttgagtgaca   2160
tgcaaagtaa gtatgatctc aatggttcgt tctcatggct cacgcaaaaa caacgaacca   2220
cactagagaa catactggct aaatacggaa ggatctgagg ttcttatggc tcttgtatct   2280
atcagtgaag catcaagact aacaaacaaa agtagaacaa ctgttcaccg ttacatatca   2340
aagggaaaac tgtccatatg cacagatgaa aacggtgtaa aaaagataga tacatcagag   2400
cttttacgag ttttttggtgc attcaaagct gttcaccatg aacagatcga caatgtaaca   2460
gatgaacagc atgtaacacc taatagaaca ggtgaaacca gtaaaacaaa gcaactagaa   2520
catgaaattg aacacctgag acaacttgtt acagctcaac agtcacacat agacagcctg   2580
aaacaggcga tgctgcttat cgaatcaaag ctgccgacaa cacgggagcc agtgacgcct   2640
cccgtgggga aaaatcatg  gcaattctgg aagaaatagc gctttcagcc ggcaaaccgg   2700
ctgaagccgg atctgcgatt ctgataacaa actagcaaca ccagaacagc ccgtttgcgg   2760
gcagcaaaac ccgtgggaat taattcccct gctcgcgcag gctgggtgcc aagctctcgg   2820
gtaacatcaa ggcccgatcc ttggagccct tgccctcccg cacgatgatc gtgccgtgat   2880
```

-continued

```
cgaaatccag atccttgacc cgcagttgca aaccctcact gatccgcatg cccgttccat    2940
acagaagctg ggcgaacaaa cgatgctcgc cttccagaaa accgaggatg cgaaccactt    3000
catccggggt cagcaccacc ggcaagcgcc gcgacggccg aggtcttccg atctcctgaa    3060
gccagggcag atccgtgcac agcaccttgc cgtagaagaa cagcaaggcc gccaatgcct    3120
gacgatgcgt ggagaccgaa accttgcgct cgttcgccag ccaggacaga atgcctcga     3180 cttcgctgct gcccaaggtt gccgggtgac gcacaccgtg gaaacggatg aaggcacgaa    3240
cccagtggac ataagcctgt tcggttcgta agctgtaatg caagtagcgt atgcgctcac    3300
gcaactggtc cagaaccttg accgaacgca gcggtggtaa cggcgcagtg gcggttttca    3360
tggcttgtta tgactgtttt tttggggtac agtctatgcc tcgggcatcc aagcagcaag    3420
cgcgttacgc cgtgggtcga tgtttgatgt tatggagcag caacgatgtt acgcagcagg    3480
gcagtcgccc taaaacaaag ttaaacatca tgagggaagc ggtgatcgcc gaagtatcga    3540
ctcaactatc agaggtagtt ggcgtcatcg agcgccatct cgaaccgacg ttgctggccg    3600
tacatttgta cggctccgca gtggatggcg gcctgaagcc acacagtgat attgatttgc    3660
tggttacggt gaccgtaagg cttgatgaaa caacgcggcg agctttgatc aacgaccttt    3720
tggaaacttc ggcttcccct ggagagagcg agattctccg cgctgtagaa gtcaccattg    3780
ttgtgcacga cgacatcatt ccgtggcgtt atccagctaa gcgcgaactg caatttggag    3840
aatggcagcg caatgacatt cttgcaggta tcttcgagcc agccacgatc gacattgatc    3900
tggctatctt gctgacaaaa gcaagagaac atagcgttgc cttggtaggt ccagcggcgg    3960
aggaactctt tgatccggtt cctgaacagg atctatttga ggcgctaaat gaaaccttaa    4020
cgctatggaa ctcgccgccc gactgggctg gcgatgagcg aaatgtagtg cttacgttgt    4080
cccgcatttg gtacagcgca gtaaccggca aaatcgcgcc gaaggatgtc gctgccgact    4140
gggcaatgga gcgcctgccg gcccagtatc agcccgtcat acttgaagct agacaggctt    4200
atcttggaca agaagaagat cgcttggcct cgcgcgcaga tcagttggaa gaatttgtcc    4260
actacgtgaa aggcgagatc accaaggtag tcggcaaata atgtctaaca attcgttcaa    4320
gccgacgccg cttcgcggcg cggcttaact caagcgttag atgcactaag cacataattg    4380
ctcacagcca aactatcagg tcaagtctgc ttttattatt tttaagcgtg cataataagc    4440
cctacacaaa ttgggagata tatcatgaaa ggctggcttt tcttgttat cgcaatagtt    4500 ggcgaagtaa tcgcaacatc cgcattaaaa tctagcgagg ctttacta                4549
```

<210> SEQ ID NO 21
<211> LENGTH: 199
<212> TYPE: DNA
<213> ORGANISM: Streptomyces sp.

<400> SEQUENCE: 21

```
gaattcacta gtcgatctgt gctgtttgcc acggtatgca gcaccagcgc gagattatgg     60
gctcgcacgc tcgactgtcg gacgggggca ctggaacgag aagtcaggcg agccgtcacg    120
cccttgacaa tgccacatcc tgagcaaata attcaaccac taaacaaatc aaccgcgttt    180
cccggaggta accaagctt                                                 199
```

<210> SEQ ID NO 22
<211> LENGTH: 46
<212> TYPE: DNA
<213> ORGANISM: Artificial Sequence
<220> FEATURE:
<223> OTHER INFORMATION: Primer

```
<400> SEQUENCE: 22
taagcttagg agcatcccat gagtgatgaa cgctaccaac agcgtc                    46

<210> SEQ ID NO 23
<211> LENGTH: 37
<212> TYPE: DNA
<213> ORGANISM: Artificial Sequence
<220> FEATURE:
<223> OTHER INFORMATION: Primer

<400> SEQUENCE: 23
caattcctgc agttaataat cgatccctat ctgcgct                              37

<210> SEQ ID NO 24
<211> LENGTH: 46
<212> TYPE: DNA
<213> ORGANISM: Artificial Sequence
<220> FEATURE:
<223> OTHER INFORMATION: Primer

<400> SEQUENCE: 24
taagcttagg agcatcccat gagtgatgaa cgttatcagc agcgcc                    46

<210> SEQ ID NO 25
<211> LENGTH: 37
<212> TYPE: DNA
<213> ORGANISM: Artificial Sequence
<220> FEATURE:
<223> OTHER INFORMATION: Primer

<400> SEQUENCE: 25
caattcctgc agttaataat caattcccat ctgcgct                              37

<210> SEQ ID NO 26
<211> LENGTH: 6
<212> TYPE: PRT
<213> ORGANISM: P.denitrificans

<400> SEQUENCE: 26

Met Glu Lys Thr Arg Leu
1               5
```